United States Patent [19]

VanRheenen

[11] Patent Number: 4,567,001
[45] Date of Patent: Jan. 28, 1986

[54] 16-METHYLENE-17α-HYDROXY-PROGESTERONES

[75] Inventor: Verlan H. VanRheenen, Portage, Mich.

[73] Assignee: The Upjohn Company, Kalamazoo, Mich.

[21] Appl. No.: 501,032

[22] Filed: Jun. 3, 1983

Related U.S. Application Data

[63] Continuation of Ser. No. 419,668, Sep. 20, 1982, abandoned.

[51] Int. Cl.$^4$ .............................. C07J 5/00; C07J 1/00
[52] U.S. Cl. ............................... 260/397.3; 260/397.4; 260/397.45
[58] Field of Search .............. 260/397.45, 397.3, 397.4

[56] References Cited

U.S. PATENT DOCUMENTS

| | | | |
|---|---|---|---|
| 3,168,537 | 2/1965 | Oliveto et al. | 260/397.4 |
| 3,275,666 | 9/1966 | Siegmann | 260/397.5 |
| 3,359,287 | 12/1967 | Babcock et al. | 260/397.4 |
| 3,689,512 | 9/1972 | Shah et al. | 260/397.5 |
| 3,759,961 | 9/1973 | Wieske et al. | 260/397.4 |

FOREIGN PATENT DOCUMENTS 1195747  7/1961  Fed. Rep. of Germany ... 260/397.4

*Primary Examiner*—Albert L. Roberts
*Attorney, Agent, or Firm*—Bruce Stein

[57] ABSTRACT

16-Methylene-17-keto steroids (III) are transformed to the corresponding 16-methylene-17α-hydroxyprogesterones (VII) which are intermediates useful in the production of betamethasone, diflorasone diacetate and melengesterol acetate.

79 Claims, No Drawings

16-METHYLENE-17α-HYDROXY-PROGESTERONES

CROSS REFERENCE TO RELATED APPLICATIONS

This is a continuation-in-part of co-pending application Ser. No. 419,668, filed Sept. 20, 1982, now abandoned.

BACKGROUND OF THE INVENTION

16-Methylene steroids are well known chemically in the estrone (aromatic A ring) series, see U.S. Pat. Nos. 3,257,429 and 3,275,666; in the corticoid series, see U.S. Pat. Nos. 3,157,679, 3,878,228, 3,354,184, 3,493,558 and 3,376,294; and in the progesterone series, see U.S. Pat. Nos. 3,168,537, 3,157,679, 3,284,476, 3,328,432 and 3,359,287. In the androstane series, see U.S. Pat. Nos. 3,641,069 and 3,300,521; Gazz, Chim. Ital. 91, 672 (1961); Hungarian Pat. No. 019,495; and U.S. patent application Ser. No. 349,490, filed Feb. 17, 1982.

Steroids with a 17α-ethynyl-17β-hydroxy group are well known to those skilled in the art and are referred to as ethisterone type steroids. These propargyl alcohols are known with methyl substitution at the C-16 position. For example, U.S. Pat. No. 4,041,055 discloses various 16α-methyl and 16β-methyl ethisterones but no 16-methylene ethisterones, see Examples 23, 24, 26, 29 and 43. U.S. Pat. No. 3,231,702, generically discloses 16(α and β)-substituted 17α(haloethynyl)-17β-hydroxy steroids.

Processes to transform 17-keto steroids to the corresponding 17α-ethynyl-17β-hydroxy steroid by reacting the 17-keto steroid with acetylene or acetylene salts in the presence of a base are well known to those skilled in the art, see for example U.S. Pat. Nos. 4,041,055 (Preparation 1), 3,441,559, 3,972,906, 3,759,961, 3,734,935, 3,689,512, etc.

In 17α-hydroxyprogesterones, the 17-hydroxy group is α and the acetyl group is β. The unnatural or opposite configuration (17β-hydroxy-17α-acetyl), as in the 17β-hydroxy steroids (V), is also known, see for example Fried & Edwards Vol II, p. 135 No. 5 and Helv. Chim. Acta 26,680 (1943).

The conversion of ethisterone type steroids to 17βhydroxy-17α-acetyl type steroids by use of mercury compounds is known, see M. W. Goldberg, Helv. Chim. Acta 26, 680 (1943). That paper, published almost 40 years ago, erroneously reports 17β-hydroxy as 17α-hydroxy. None of the compounds in Goldberg's paper have any substitution at the C-16 position. U.S. Pat. No. 4,102,908 discloses a process for transformation of the nitrate ester of ethisterone type compounds to 17α-hydroxyprogesterones. None of the compounds exemplified in U.S. Pat. No. 4,102,908 have any substitution at the C-16 position.

Steroidal sulfoxides are known, see for example U.S. Pat. Nos. 4,041,055 and 4,342,702. In U.S. Pat. No. 4,041,055, the sulfoxide is a 20-methoxy-21-(phenylsulfinyl)-Δ$^{17(20)}$ steroid. In U.S. Pat. No. 4,342,702, the sulfoxide is a 21-chloro-20-methoxy-21-(phenylsulfinyl)-Δ$^{17(20)}$ steroid. The sulfoxide of the present invention, the 16-(phenylsulfinylmethyl)-Δ$^{16}$ steroid (VI) is readily transformed to a 16-methylene-17α-hydroxyprogesterone (VII). The prior art sulfoxides of U.S. Pat. No. 4,041,055 produce 16-methyl(α and β) substituted 17α-hydroxyprogesterones but not the desired 16-methylene-17α-hydroxyprogesterones of the present invention. Likewise, the prior art sulfoxides of U.S. Pat. No. 4,342,702 produce 21-halo-16-methyl(α or β) substituted 17α-hydroxyprogesterones but not the desired 16-methylene-17α-hydroxyprogesterones of the present invention. This is extremely important, because even though the 16-methylene-17α-hydroxyprogesterones (VII) of the present invention can be transformed to the 16-methyl-17α-hydroxyprogesterones of U.S. Pat. No. 4,041,055 and the 21-halo-16-methyl-17α-hydroxyprogesterones of U.S. Pat. No. 4,342,702, the 16-methylene group is necessary for production of melengestrol acetate (17α-acetyloxy-6-methyl-16-methylenepregna-4,6-diene-3,20-dione), and therefore melengestrol acetate cannot be produced from the prior art sulfoxides.

U.S. Pat. No. 4,041,055 discloses a process for the transformation of an ethisterone type steroid to the corresponding sulfoxide by use of a sulfenylating agent. That reaction proceeds via an allene sulfoxide intermediate. Likewise, U.S. Pat. No. 4,342,702 transforms a halo substituted ethisterone type steroid to the corresponding 21-halo substituted sulfoxide by use of a sulfenylating agent via a 21-halo allene sulfoxide. The sulfenylation reaction of the present invention does not proceed via an allene sulfoxide intermediate.

16-Methylene-17α-hydroxyprogesterones are known. See, for example, J. Chem. Soc. 2385 (1960) and U.S. Pat. Nos. 3,040,069, 3,130,209, 3,157,679, 3,168,537, 3,284,476 and 3,359,287. In U.S. Pat. No. 3,359,287 the compound of formula (X) is the closest to the compound of formula (VIIB). Similarly the compound of formula (VI) of U.S. Pat. No. 3,359,287 is the closest compound to the 16-methylene-17α-hydroxyprogesterone (VIIC). However, U.S. Pat. No. 3,359,287 requires both substituents at C-11 to be hydrogen atoms which is significantly different from the functionalized C-11 positions in the compounds of the present invention. None of these 16-methylene-17α-hydroxyprogesterones were produced from a sulfoxide by reaction with a thiophile as in the present invention.

16-Methylene corticoids are known, see U.S. Pat. No. 3,115,508. The 16-methylene corticoids disclosed were 5α or saturated A-ring corticoids. The 16-methylene corticoids of the present invention have unsaturation in the A or B-rings.

U.S. Pat. No. 4,041,055 claims a process for transforming a 16α- or 16β-methyl-17-keto steroid to the corresponding 16(α or β)-methyl-17α-hydroxyprogesterone. The process involved ethynylating the 17-keto steroid to produce a 17α-ethynyl-17β-hydroxy steroid which was then sulfenylated to form an allene sulfoxide. Michael addition to the allene sulfoxide produced the corresponding sulfoxide. Reaction of the sulfoxide with a thiophile produced a 17α-hydroxy-20-alkoxy-20-unsaturated steroidal side chain which upon acid hydrolysis produced the 17α-hydroxyprogesterone side chain. U.S. Pat. No. 4,041,055 discloses that if one starts with a 16α- or 16β-methyl 17-keto steroid, one then following the above process produces the corresponding 16α- or 16α-methyl-17α-hydroxyprogesterone. U.S. Pat. No. 4,041,055 makes absolutely no mention of 16-methylene substitution. In addition the process and intermediates of the present invention are quite different than those of U.S. Pat. No. 4,041,055.

U.S. Pat. No. 4,342,702 discloses a process for the transformation of a 16(α or β)-methyl-17-keto steroid to a 21-halo-16(α or β)-methyl-17α-hydroxypregnane by converting the 17-keto starting material to a halogen substituted ethisterone type steroid by use of a halogenated acetylene. The halogen substituted ethisterone type steroid is reacted with a sulfenylating agent to form a 21-halo allene sulfoxide which is converted to the corresponding 21-halo sulfoxide and ultimately to the 21-halo-16($\alpha$ or $\beta$)-methyl-17$\alpha$-hydroxyprogesterone.

SUMMARY OF THE INVENTION

Disclosed are the 17$\alpha$-ethynyl steroids (IV), 17$\beta$-hydroxy steroids (V), sulfoxides (VI), 16-methylene-17$\alpha$-hydroxyprogesterones (VII) and 16-methylene corticoids (IX).

Disclosed is a process for the preparation of a $C_3$ protected 17$\alpha$-ethynyl steroid (IVA) which comprises contacting a $C_3$ protected 16-methylene-17-keto steroid (IIIA) with an excess of monolithium acetylide previously cooled to about 20° or less, maintaining the reaction mixture temperature of less than $-20°$, and contacting the mixture with a quenching agent. Also disclosed is a process for the preparation of a 17$\alpha$-ethynyl steroid (IVA) which comprises performing the first 3 steps above, and then contacting the reaction mixture of step 3 with a proton source.

Disclosed is a process for the preparation of a 17$\alpha$-ethynyl steroid (IVB) which comprises contacting a 16-methylene-17-keto steroid (IIIB) with an excess of monolithium acetylide previously cooled to about $-20°$ or less, maintaining the reaction mixture temperature at less than $-20°$, and contacting the reaction mixture with a quenching agent.

Also disclosed is a process for the preparation of a 17$\alpha$-ethynyl steroid (IVC) which comprises contacting a $C_3$ protected 16-methylene steroid (IIIC) with an excess of monolithium acetylide previously cooled to about $-20°$ or less, maintaining the reaction mixture temperature at less than $-20°$, and contacting the reaction mixture of step 3 with a means for hydrolyzing the $C_3$ protecting group.

Disclosed is a process for the preparation of a 17$\beta$-hydroxy steroid (V) which comprises contacting a 17$\alpha$-ethynyl steroid (IV) with a mercuric agent.

Also disclosed is a process for the preparation of a sulfoxide (VI) which comprises contacting a 17$\beta$-hydroxy steroid (V) in a solvent containing a weak base or tertiary amine at a temperature of less than 0° with a sulfenylating agent ($R_5$-S-M).

Further disclosed is a process for the preparation of a 16-methylene-17$\alpha$-hydroxy steroid (VII) which comprises contacting a sulfoxide (VI) with a thiophile at a temperature of greater than 30° under pressure.

DETAILED DESCRIPTION OF THE INVENTION

The 16-methylene-17-keto steroid (III) starting materials are well known to those skilled in the art. See, for example, U.S. Pat. Nos. 3,275,666, 3,300,521 and 3,641,069, Gazz. Chim. Ital. 91, 672 (1961), Hungarian Pat. No. 019,495 and U.S. patent application Ser. No. 349,490, filed Feb. 17, 1982.

It is preferred that the 16-methylene-17-keto steroid (III) starting materials be prepared by conversion of a 17-keto steroid (I) to a 16-methylene-17-keto steroid (III) via a 16-substituted steroid intermediate (II), see Chart A. The process can be performed two different ways: (1) with isolation of the 16-substituted intermediate (II), and (2) without isolation of the 16-substituted intermediate (II). In the first case, the 17-keto steroid (I) is reacted with a $C_{16}$ activating agent in the presence of a strong base, the intermediate (II) is isolated and reacted with a formaldehyde generating agent in the presence of a base. In the second case, after the 16-substituted intermediate (II) is generated, the formaldehyde generating agent is added without additional base. These two processes are considered the equivalent of each other.

The 17-keto steroid (IA-IC), or as the $C_3$ protected form, is reacted with a $C_{16}$ activating agent in the presence of an enolizing base. The $C_{16}$ activating agent is a compound which when reacted with a 17-keto steroid (I) and an enolizing base activates the $C_{16}$ position of the 17-keto steroid (I) so as to make it reactive to the addition of formaldehyde. $C_{16}$ activating agents include compounds of the formula X—CO—R where R is a hydrogen atom or an electron withdrawing group such as a trifluoromethyl group, cyano group or $COOR_{16}$. The leaving group, X, is $OR_b$, or a chlorine, bromine or iodine atom. It is preferred that the $C_{16}$ activating group is selected from the group consisting of oxylal esters (such as methyl and ethyl oxylate), formyl esters (such as methyl or ethyl formate), trifluoroacetate esters (such as methyl or ethyl trifluoroacetate).

The enolizing base is a base sufficiently strong to form an enolate at $C_{17}$ and in conjunction with a $C_{16}$ activating agent form a 16-substituted intermediate (II). Generally the enolizing base is a strong base which has a pK of greater than 12. It is preferred that the enolizing base be selected from the group consisting of metal-ORb, metal hydride, or metal amides. Metal refers to lithium, sodium, potassium or magnesium, and Rb is alkyl of 1 thru 5 carbon atoms or phenyl. Enolizing bases include, for example, sodium methoxide, potassium ethoxide, sodium hydride, or lithium diisopropylamide. It is preferred that the metal is sodium and the base is sodium methoxide or sodium ethoxide. The reaction should be performed in an inert solvent, preferably selected from solvents such as toluene, methylene chloride, THF, but may also be performed in alcohols such as methanol, ethanol, etc. The reaction should be performed under an inert atmosphere, preferably nitrogen, in a temperature range of about $-20°$ to about 50°.

The reaction is monitored by TLC as is well known to those skilled in the art. When the reaction is complete, the 16-substituted steroid (IIA-IID) can be isolated (Example 1) or can be reacted in situ (Example 3 and 4) to produce the desired 16-methylene steroid (III).

In either event, formaldehyde or a formaldehyde generating agent is then added. Before the formaldehyde generating agent is added, it is important to neutralize all the excess enolizing base. This is preferably done by the addition of an acid such as acetic acid or hydrochloric acid (Example 1). A formaldehyde generating agent is a compound which, when used or reacted, acts as, or generates formaldehyde (HCHO) so that the formaldehyde generating agent could be formaldehyde itself or a compound or polymer which produces formaldehyde in situ or acts as formaldehyde. It is preferred that the formaldehyde generating agent be selected from the group consisting of formaldehyde, paraformaldehyde, trioxane and an aqueous or alcoholic solution of formaldehyde. It is more preferred that the formaldehyde generating agent be paraformaldehyde or an aqueous solution of formaldehyde. In the event that the 16-substituted steroid (II) is not isolated and the reaction is being performed as a one-pot process, the reaction mixture is sufficiently basic to cause the transformation of the 16-substituted steroid (II) to the 16-methylene steroid (III). If the reaction is being performed as a two-pot process with isolation of the 16-substituted steroid (II) intermediate, the second step requires that a base be added. There may be a strong base such as $OR_b$ or a weak base such as tertiary amines. Preferred weak bases include, for example, triethylamine, tributylamine, or pyridine. Triethylamine is the preferred weak base. The reaction should be performed in an inert solvent such as the first step. The weak base can serve as solvent or cosolvent. The reaction is performed under an inert atmosphere, preferably nitrogen, in a temperature range of 0° to reflux. The reaction is monitored by TLC as is well known to those skilled in the art and is complete in 0.25 to 6 hr, usually about 1 hr, depending on temperature, etc. When complete, the 16-methylene steroid (III) is isolated and purified by means well known to those skilled in the art.

If the 16-methylene steroid (III) is obtained in a $C_3$ protected form, the $C_3$ protecting group is readily removable and the A ring functionality is readily convertible to the unprotected form identified by formulas (A–C) by means well known to those skilled in the art.

The 16-methylene-17-keto steroid (IIIA–IIIC) starting materials may have variable substituents at positions 1, 6, 9, 10 and 11, as is well known to those skilled in the art. For example, U.S. Pat. No. 4,416,821, discloses 16-methylene-17-keto steroids with $\Delta^1$, 6-fluoro, 6-methyl, 11$\beta$-hydroxy, 11-keto, 11$\alpha$-hydroxy $\Delta^{9(11)}$, 9$\beta$,11$\beta$-epoxy, and 9$\alpha$-fluoro substitution as well as combinations thereof. It is preferred that $R_{10}$ is methyl. It is preferred in the $\Delta^4$-3-keto series (A) that $R_6$ be a hydrogen atom, methyl or methylene group but in the $\Delta^{1,4}$-3-keto series (B) that $R_6$ be a hydrogen or fluorine atom.

The 16-methylene-17-keto steroids (IIIA–IIIC) are converted to the corresponding 17$\alpha$-ethynyl steroids (IVA–IVC) by reaction with an appropriate reactive form of acetylene. In the present case the active acetylene agent, monolithium acetylide can be prepared by the process described by M. M. Midland in J. Org. Chem. 40, 2250 (1975). The $LiC_2H$ is prepared in a dry ether solvent such as THF, dioxane, diethyl ether, dimethyl ether at a temperature of less than $-20°$, preferably about $-20°$ to $-80°$, more preferably at about $-60°$. Alternatively and preferably the mono and lithium acetylide is generated in situ as more fully described infra and Example 33.

The 16-methylene-17-keto steroids (IIIA–IIIC) may or may not have to have the functionality at $C_3$ protected during the ethynylation reaction depending on the nature of the steroid a ring (A–C), see Chart B. For the $\Delta^4$-3-keto steroids (A) the $C_3$ ketone is protected as the enol ether (Aa), ketal (Ab), enamine (Ac) or enol ester as is well known in the art, see Chart C. $R_3$ is alkyl of 1 thru 5 carbon atoms, with the proviso that for the ketal (b) its $R_3$'s can be connected. The preferred enol ether (Aa) is the methyl or ethyl ether. The preferred ketal (Ab) is the ethylene ketal. For the enamine (Ac) $R_3'$ and $R_3''$ are alkyl of 1 thru 5 carbon atoms; $R_3'$ and $R_3''$ may be the same or different and the $R_3'$ and $R_3''$ can be connected. The preferred enamines are selected from the group consisting of pyrrolidine, morpholine and diethylamino amines. The enol ethers (a) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The ketals (b) are also prepared by well known methods, see Steroid Reactions, supra, page 11–14. The 3-enamines (c) are also prepared by methods well known in the art, see U.S. Pat. No. 3,629,298 and Steroid Reactions, supra, page 49–53.

The $\Delta^{1,4}$-3-keto steroid (B) do not have to have the $C_3$ ketone protected. The 3-hydroxy steroid (C) should have the 3$\beta$-hydroxyl group protected as the ether (Ca) or ester (Cb), see Chart B'. The preferred blocking groups are the methyl and ethyl enol ethers (Aa), ethylene ketal (Ab), pyrrolidine enamine (Ac), methyl ester (Co) and acetate ester (Cb).

The $C_3$ protected forms (Aa, Ab and Ac) of the $\Delta^4$-3-keto steroids (A) and its $C_3$ protected forms (Ca and Cb) of the 3$\beta$-hydroxy steroids (C) are considered equivalent to the non-protected or free form (A and C) respectively since the $C_3$ protecting groups are readily removable to convert the $C_3$ protected forms (Aa, Ab, Ac, Ca and Cb) to (A and C) respectively.

The monolithium acetylide and the 16-methylene-17-keto steroids (IIIAa, IIIAb, IIIAc, IIIB, IIICa and IIICb) are contacted slowly at a temperature of less than $-20°$ C., preferably about $-20°$ to $-70°$. At least 1.5 equivalents of monolithium acetylide are used. When the reaction is complete the excess acetylide is quenched or destroyed by reaction with a quenching agent which is any aqueous system such as water, saline or aqueous buffers depending on what final pH is desired. The preferred quenching agent is phosphate buffer. The 17$\alpha$-ethynyl steroids (IV) are obtained or isolated from the reaction mixture by means well known to those skilled in the art. In the case of the $\Delta^4$-3-keto steroids (A) and 3-hydroxy steroid (C) the 17$\alpha$-ethynyl steroid (IV) is isolated as the $C_3$ protected form (Example 24). The $C_3$ protecting group is removed by means well known to those skilled in the art or the $C_3$ protecting group may be left on for further chemical modification of the 17$\alpha$-ethynyl steroid (IV) as in Example 25. Before the 17$\alpha$-ethynyl steroid (IV) is isolated the $C_3$ protecting group can be hydrolyzed in situ so as to obtain the unprotected or free 17$\alpha$-ethynyl steroid (IVA, IVC) by reaction with a proton source such as sulfuric acid or hydrochloric acid. For example, if the 16-methylene-17-keto steroid (IIIA) is protected as the enol ether (a) the protecting group can be removed by acid so that the 17$\alpha$-ethynyl steroid (IV) will be isolated in the free $\Delta^4$-3-keto from (A), see Examples 11 and 19. The $\Delta^{1,4}$-3-keto steroids (B) are not protected and therefore the 17$\alpha$-ethynyl product (IVB) will be in the free or unprotected form. The $C_3$ protecting group is removed from the 3-hydroxy steroids (C) by reaction with a means for hydrolyzing the $C_3$ protecting group which in the case of the ethers (Ca) includes acids with a pKa of less than 4.0 and in the case of esters (Cb) includes bases such as sodium or potassium hydroxide, carbonate, or bicarbonate. Alternatively and preferably the monolithium acetylide is generated in situ. Operationally, this is much easier, and the reaction may be performed at about $-20°$ rather than at $-60°$ when the reagent is prepared separately. Using the in situ method an alkali metal amide base such as lithium diethylamide, lithium diisopropylamide and equivalent bases well known to those skilled in the art are prepared by reacting the appropriate amine with an organo-lithium reagent such as n-butyl lithium or phenyl lithium. An acetylene saturated solution is added to an ether solvent (THF, diethyl ether and dioxane), containing the appropriate form of the 16-methylene-17-keto steroid (IIIA–IIIC) at about $-20°$. The lithium amide is then added to the mixture of 16-methylene-17-keto steroid (III) and acetylene in the ether solvent. The reaction is stirred at about −40° until complete as measured by TLC usually 0.5-2 hr. The reaction mixture is slowly added to a saline/water (1/1) mixture and then worked up in the usual manner.

The 17α-ethynyl steroid (IVA-IVC) is transformed to the corresponding 17β-hydroxy steroid (VA-VC) by reaction with a mercuric agent. Oxymecuration of ethisterone derivatives is old, see Helv. Chim. Acta. 26, 680 (1943). However, the present D ring is not a simple ethesterone derivative. Here the 17α-ethynyl-17β-hydroxy substituents are allylic to a 16-methylene group. In the present invention surprisingly and unexpectedly quantitative yields of the 17β-hydroxy steroids (VA-VC) are obtained indicating that its allylic alcohol system did not compete with the propargyl alcohol system in the oxymercuration.

The mercuric agent can be produced by reaction of mercuric oxide with a strong acid such as sulfuric, hydrochloric, or nitric acid. The mercuric salts, mercuric sulfate, mercuric chloride or mercuric nitrate can be used directly in acid medium. Mercuric sulfate or this salt made from mercuric oxide and sulfuric acid is preferred. A catalytic amount of a mercuric agent and 17α-ethynyl steroid (VA-VC) are contacted at 20°-65° for 2-24 hr in an aqueous polar solvent. When the oxymercuration reaction is complete, the reaction mixture is filtered (thru Celite) to remove insoluble mercuric salt solids and the 17β-hydroxy steroid (VA-VC) is recovered from the filtrate by means well known to those skilled in the art. Alternatively the oxymercuration reaction can be performed using the mercuric agent affixed to a resin. See M. S. Newman, J. Am. Chem. Soc., 75, 4740 (1953).

The 17β-hydroxy steroids (VA-VC) are next converted to the corresponding sulfoxides (VIA-VIC) by reaction with a sulfenylating agent of the formula $R_{22}$—S—M (XII). It is preferred that M is a chlorine or bromine atom, more preferred that M be a chlorine atom. It is preferred that $R_{22}$ be methyl, phenyl, p-chlorophenyl, p-methoxyphenyl or p-methylphenyl. It is more preferred that $R_{22}$ be phenyl.

The appropriately substituted sulfenylating agents (XII) are prepared by methods known to those skilled in the art. For example, sulfuryl chloride is added to a thiol previously dissolved in an organic solvent such as carbon tetrachloride. See Chem. Reviews, 39, 269 (1946) at page 279 and U.S. Pat. No. 2,929,820.

The sulfenylation reaction is carried out in a non-polar aprotic solvents such as toluene, chloroform, diethyl ether, or methylene chloride, THF, and dioxane or mixtures thereof. It is preferred that the solvent be methylene chloride. The reaction is carried out in the presence of at least an equal molar amount of a tertiary amine base, such as triethylamine, trimethylamine or pyridine. Trimethylamine is preferred. Any excess base serves as additional solvent for the reaction. The reaction is preferably carried out under an inert dry gas such as nitrogen, argon, or carbon dioxide. The substituted sulfenyl halide (XII) is added dropwise to the reaction mixture at a temperature of −20° to −40°. Following addition of the substituted sulfenylating agent (XII) to the reaction mixture, the excess substituted sulfenylating agent is quenched with an appropriate quenching agent such as water, cyclohexane, various alcohols such as methanol and ethanol, or acetone. The sulfoxide (VII) may be obtained by standard work-up.

The sulfoxide (VI) exists as 2 double bond isomers; the compound of formula (VI) and where the unsaturation is between $C_{16}$ and the carbon atom attached to the sulfur atom. The endocyclic isomer (VI) greatly predominates with only trace amounts of the exocyclic isomer. However, the ratio of the isomeric sulfoxides is unimportant for the purposes of the present invention as both isomers are converted to the same product in the next step.

The sulfoxides (VIA-VIC) are converted to the corresponding 16-methylene-17α-hydroxyprogesterones (VIIA-VIIC) by reaction with a thiophile with heat. The sulfoxides (VIA-VIC) are placed in an appropriate solvent or mixture of solvents such as toluene, methanol, ethylene dichloride or acetone. Some thiophiles such as hydroxide, alkoxide, etc. produce undesirable side reactions; others such as trimethylphosphite and diethylamine and mixtures thereof are more suitable. The preferred thiophile is trimethylphosphite. Trimethylphosphite is known as a thiophile, see D. A. Evans & G. C. Andrews, Acct. of Chem. Res. 7, 147 (1974) at p. 150. The sulfoxide (VIA-VIC) and thiophile are contacted and heated from about 50°-100° depending on solvent(s), sulfoxide (VIA-VIC), thiophile, and whether or not the reaction is conducted under pressure. It is preferred to heat the reaction mixture from 60°-110° in a sealed reacting container for 4-24 hr. When the reaction is complete the 16-methylene-17α-hydroxyprogesterone (VIIA-VIIC) is isolated and purified by means well known to those skilled in the art.

The 16-methylene-17α-hydroxyprogesterones steroids (VIIA-VIIC) are useful as intermediates in the production of commercial pharmaceutical agents in two ways. First, 16-methylene steroids are intermediate in the manufacture of certain progestational agents such as melengestrol acetate, and second where the 16-methylene group is reduced to 16α-methyl or 16β-methyl to give intermediates useful in the production of anti-inflammatory corticoids. For example, androstenedione can be converted to melengestrol acetate, a 16-methylene steroid in the following manner: (1) androstenedione (IA) is converted to 6-methyleneandrost-4-ene-3,17-dione by the process of U.S. Pat. No. 3,642,840, Example 18; (2) 6-methyleneandrost-4-ene-3,17-dione is converted to 6-methylandrosta-4,6-diene-3,17-dione (IA) by the process of U.S. Pat. No. 3,117,966, Example 16; (3) 6-methylandrosta-4,6-diene-3,17-dione is converted to 6-methyl-16-methyleneandrosta-4,6-diene-3,17-dione (IIIA) by the process of Hungarian Pat. No. 019,495, Gazz. Chim. Ital. 91, 672 (1961) or the above described process for transformation of a 17-keto steroid to the corresponding 16-methylene-17-keto steroid (U.S. patent application Ser. No. 349,490, filed Feb. 17, 1982); (4) 6-methyl-16-methyleneandrosta-4,6-diene-3,17-dione (IIIA) is converted to 17α-hydroxy-6-methyl-16-methylenepregna-4,6-diene-3,20-dione (VIIA') by the process of the present invention, Examples 20-23; and (5) acylation of the 17α-hydroxy-6-methyl-16-methylenepregna-4,6-diene-3,20-dione (VIIA') to 17-acetyloxy-6-methyl-16-methylenepregna-4,6-diene-3,20-dione (melengesterol acetate, VIII) by the process of U.S. Pat No. 4,154,748, Example 12, see Chart E.

Alternatively, the following sequence can be used: (1) 16-methyleneandrostenedione (IIIA, Hungarian Pat. No. 019,495, Example 3) is converted to 17α-ethynyl-3,17β-dihydroxy-16-methyleneandrosta-3,5-diene 3-methyl ether by the process of the present invention, Example 24, then (2) the 17α-ethynyl-3,17β-dihydroxy- 16-methyleneandrosta-3,5-diene 3-methyl ether is converted to 17α-ethynyl-17β-hydroxy-6,16-dimethyleneandrost-4-en-3-one by the process of U.S. Pat. No. 3,642,840, (3) the 17α-ethynyl-17β-hydroxy-6,16-dimethyleneandrost-4-en-3-one (IVA) is then converted by the process of the present invention, Examples 27–29, to the corresponding 17β-hydroxy steroid (VA), 16-unsaturated steroid (VIA) and ultimately to 17α-hydroxy-6,16-dimethylenepregn-4-ene-3,20-dione (VIIA″), which upon reaction with acetic anhydride and p-TSA (Examples 32 & 42) forms 17α-acetyloxy-6-methyl-16-methylenepregna-4,6-diene-3,20-dione, melengestrol acetate (VIII), see Chart E.

Preferably, the following sequence is used (1) 3-methoxy-16-methyleneandrosta-3,5-dien-17-one (IIIAa, Example 8) is converted to 17α-ethinyl-17β-hydroxy-16-methyleneandrost-4-en-3-one (IVA) by the process of Example 36, then (2) the 17α-ethinyl-17β-hydroxy-16-methyleneandrost-4-en-3-one (IVA) is converted to 17α-acetyl-17β-hydroxy-16-methyleneandrost-4-en-3-one (VA) by the process of Example 37, (3) the 17α-acetyl-17β-hydroxy-16-methyleneandrost-4-en-3-one (VA) is converted to 16-(phenylsulfinylmethyl)pregna-4,16-diene-3,20-dione by the process of Example 38, (4) the 16-(phenylsulfinylmethyl)pregna-4,16-diene-3,20-dione (VIA) is converted to 17α-hydroxy-16-methylenepregn-4-ene-3,20-dione (VIIA) by the process of Example 39, (5) the 17α-hydroxy-16-methylenepregn-4-ene-3,20-dione (VIIA) is converted to 17α-hydroxy-3β-methoxy-16-methylenepregna-3,5-dien-3-one (VIIAa) by the process of Example 40, (6) the 17α-hydroxy-3β-methoxy-16-methylenepregna-3,5-dien-3-one (VIIAa) is transformed into 17α-hydroxy-6,16-dimethylenepregn-4-ene-3,20-dione (VIIA″) by the process of Example 41, and finally by the process of Examples 32 or 42 the 17α-hydroxy-6,16-dimethylenepregna-4-ene-3,20-dione (VIIA″) is converted to melengestrol acetate (VIII).

Following Chart F, the 16-methylene-17α-hydroxyprogesterones (VIIA–C) can readily be transformed into a 16-methylene corticoid (IX) by reaction with iodine, an excess of calcium oxide an aqueous sodium hydroxide and potassium acetate in acetone as is well known, see for example H. J. Ringold, et al., J. Am. Chem. Soc. 80, 250 (1958), O. Halpern, et al., J. Am. Chem. Soc. 81, 439 (1959) and J. Org. Chem. 25, 1966 (1060). The 16-methylene corticoid (IX) can then be readily transformed to a 16β-methyl corticoid (X) by the process of U.S. Pat. No. 3,115,508 or to a 16α-methyl corticoid (XI) by the process of U.S. Pat. No. 3,130,209.

For example, betamethasone (9α-fluoro-11β,17α,21-trihydroxy-16β-methylpregna-1,4-diene-3,20-dione) can be prepared from 17β-hydroxy-16-methylenepregna-1,4,9(11)-triene-3,20-dione (VIIB, Example 18) by first transforming it to 17α,21-dihydroxy-16-methylenepregna-1,4,9-(11)-triene-3,20-dione 21-acetate (IX) by the process of J. Am. Chem. Soc. 80, 250 (1958) J. Am. Chem. Soc. 81, 439 (1959) and J. Org. Chem. 25, 1966 (1960) and next transforming it to 17α,21-dihydroxy-16β-methylpregna-1,4,9(11)-triene-3,20-dione 21-acetate (X) by the process of U.S. Pat. No. 3,115,508. The transformation of 17α,21-dihydroxy-16β-methylpregna-1,4-diene-3,20-dione 21-acetate to betamethasone is described in U.S. Pat. No. 3,104,246 Examples I and II.

Dexamethasone (9α-fluoro-11β,17α,21-trihydroxy-16α-methylpregna-1,4-diene-3,20-dione) can also be prepared from 17β-hydroxy-16-methylenepregna-1,4,9(11)-triene-3,20-dione (VIIB, Example 18) by first transforming it to 17α,21-dihydroxy-16-methylenepregna-1,4,9(11)-triene-3,20-dione 21-acetate (IX) as described above and next transforming it to 17α,21-dihydroxy-16α-methylpregna-1,4,9(11)-triene-3,20-dione 21-acetate (XI) by the process of U.S. Pat. No. 3,130,209. 17α,21-Dihydroxy-16α-methylpregna-1,4,9(11)-triene-3,20-dione 21-acetate (XI) is then epoxidized by means well known to those skilled in the art, see for example U.S. Pat. No. 3,980,778 Examples 2 and 7 to produce 9β,11β-epoxy-17α,21-dihydroxy-16α-methylpregna-1,4-diene-3,20-dione which is transformed to dexamethasone 21-acetate by the process of U.S. Pat. No. 3,007,923 Example 2.

Likewise diflorasone diacetate (6α,9α-difluoro-11β,17α,21-trihydroxy-16β-methylpregna-1,4-diene-3,20-dione 17,21-diacetate) can be produced using the process of the present invention. First, 6α-fluoro-11β-hydroxyandrosta-1,4-diene-3,17-dione (U.S. Pat. No. 2,867,630) is dehydrated to 6α-fluoroandrost-1,4,9(11)-triene-3,17-dione by means well known to those skilled in the art, see Steroid Reactions, C. Djerassi, Holden-Day, San Francisco, 1963 p. 238 & 239. The 16-methylene group is then added by the process of U.S. patent application Ser. No. 349,490 to produce 6α-fluoro-16-methyleneandrosta-1,4,9(11)-triene-3,17-dione (IIIB) which is converted by the process of the present invention to 6α-fluoro-17α-hydroxy-16-methylenepregna-1,4,9(11)-triene-3,20-dione (VIIB). The 21-hydroxy function of the corticoids is next introduced as described above followed by transformation of the 16-methylene group to a 16β-methyl group also described above to give 6α-fluoro-17α,21-dihydroxy-16β-methylpregna-1,4,9(11)-triene-3,20-dione 21-acetate which is acylated according to the procedure described in U.S. Pat. No. 4,154,748 (Examples 6 and 7) to produce 6α-fluoro-17α,21-dihydroxy-16β-methylpregna-1,4,9(11)-triene-3,20-dione 17,21-diacetate (U.S. Pat. No. 3,980,778, Example 6). 6α-fluoro-17α,21-dihydroxy-16β-methylpregna-1,4,9(11)-triene-3,20-dione-17,21-diacetate is then converted to diflorasone diacetate by the process of U.S. Pat. No. 3,980,778 (Examples 7 and 8).

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

Saline refers to an aqueous saturated sodium chloride solution.

p-TSA refers to p-toluenesulfonic acid.

NMR refers to nuclear (proton) magnetic resonance spectroscopy, chemical shifts are reported in ppm ($\delta$) downfield from TMS.

TMS refers to tetramethylsilane.

TEA refers to triethylamine.

When solvent pairs are used, the ratio of solvents used are volume/volume (v/v).

Androstenedione refers to androst-4-ene-3,17-dione.

M is a chlorine or bromine atom or phenylsulfone, phthalimide or imidazole group.

R is a hydrogen atom, trifluoromethyl or cyano group or $COOR_{16}$.

$R_3$ is alkyl of 1 thru 5 carbon atoms with the proviso that with the ketal (c), the $R_3$ groups can be connected.

$R_3'$ is alkyl of 1 thru 5 carbon atoms.

$R_3''$ is alkyl of 1 thru 5 carbon atoms.

$R_6$ is a hydrogen or fluorine atom, methyl or methylene group. When $R_6$ is methylene, there are no 6-7 double bonds in formula (A) or 5-6 double bonds in formula (C).

$R_9$ is nothing or a hydrogen or fluorine atom, which includes the $\Delta^{9(11)}$ and $9\beta,11\beta$-epoxide functionality.

$R_{10}$ is a hydrogen atom or methyl group.

$R_{11}$ is nothing or a hydrogen or oxygen atom, an $\alpha$-hydroxy group, or a $\beta$-hydroxy group, which includes the $\Delta^{9(11)}$ and $9\beta,11\beta$-epoxide functionality.

$R_{16}$ is alkyl of 1 thru 3 carbon atoms.

$R_{22}$ is alkyl of 1 thru 5 carbon atoms, trichloromethyl, phenyl, phenyl substituted with 1 thru 4 carbon atoms or substituted with 1 thru 3 nitro or trifluoromethyl groups, aralkyl of 7 thru 12 carbon atoms, or $-N-(R_{122})_2$.

$R_{122}$ is alkyl of 1 thru 4 carbon atoms, phenyl or phthalimide. ___ is a single or double bond. ~ indicates that the attached atom or group can be in either the $\alpha$ or $\beta$ configuration.

Metal refers to lithium, sodium, potassium or magnesium.

When the term "alkyl of ___ thru ___ carbon atoms" is used, it means and includes isomers thereof where such exist and are operable.

X is $OR_b$, or a chlorine, bromine, or iodine atom.

$R_b$ is alkyl of 1 thru 5 carbon atoms or phenyl.

A formaldehyde generating agent is a compound which, when used or reacted, acts as, or generates, formaldehyde (HCHO) so that the formaldehyde generating agent could be formaldehyde itself or a compound which produces formaldehyde in situ or acts as formaldehyde.

$C_{16}$ activating agent is a compound which, when reacted with a 17-keto steroid (I) and an enolizing base produces a 16-substituted intermediate (II) and activates the $C_{16}$ position of the 17-keto steroid (I) so as to make it reactive to the addition of formaldehyde.

An enolizing base is a base which when reacted with a 17-keto steroid (I) and a $C_{16}$ activating agent produces a 16-substituted intermediate (II).

EXAMPLES

Without futher elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

EXAMPLE 1

3-Methoxy-16-(methyloxalyl)androsta-3,5,9(11)-trien-17-one (II)

Dimethyloxalate (11.5 g) and sodium methoxide (6.5 g) was added to a mixture of 3-methoxyandrosta-3,5,9(11)-trien-17-one (I, U.S. Pat. No. 3,516,991, 17 g) and toluene (100 ml). This mixture was stirred overnight at 20°–25° under nitrogen during which time a precipitate occurred. Water, saline, methanol, and potassium hydroxide (5%) were added and, following separation of the layers, the organic layer was further washed with potassium hydroxide (5%). The aqueous layers were combined and neutralized to pH of 5 with hydrochloric acid (2N) and extracted twice with methylene chloride. The organic layers were combined and dried over sodium sulfate, filtered and the filtrate concentrated under reduced pressure to an oil which is crystallized from methanol to give the title compound. NMR (CDCl$_3$)=0.99, 1.19, 3.18, 3.60, 3.89, 5.20, 5.30 and 5.54 $\delta$.

EXAMPLE 2

3-Methoxy-16-methyleneandrosta-3,5,9(11)-trien-17-one (IIIAa)

To a mixture of 3-methoxy-16-(methyloxalyl)androsta-3,5,9(11)-trien-17-one (IIAa, Example 1, 13.9 g) in THF (125 ml) was added paraformaldehyde (1.62 g) and triethylamine (7.5 ml). The resulting mixture was refluxed for one hour at which time TLC (ethyl acetate/toluene-1/9) showed the reaction to be complete. The reaction mixture was poured into an aqueous salt solution and extracted with ethyl acetate. The organic phase was dried over sodium sulfate, filtered and concentrated under reduced pressure to give an oily residue which was crystallized from methanol to give the title compound. NMR (CDCl$_3$)=0.90, 1.13, 3.57, 5.17, 5.30, 5.40, 5.56 and 6.08 $\delta$.

EXAMPLE 3

16-(Methyloxalyl)androsta-1,4,9(11)-triene-3,17-dione (IIBA)

A 25% solution of sodium methoxide in methanol (0.252 ml) was added to a mixture of androsta-1,4,9(11)-triene-3,17-dione (IB, U.S. Pat. No. 4,216,159, Preparation 4, 282 mg), dimethyloxalate (175 mg) and methylene chloride (3 ml) at 0°. This mixture was stirred at 0° for 4.5 hrs, following which an additional 0.03 ml of methoxide solution was added, and the stirring was continued for an additional two hours. At this time, conversion to the title compound was essentially complete as measured by TLC (acetone/methylene chloride; 5/95).

EXAMPLE 4

16-Methyleneandrosta-1,4,9(11)-triene-3,17-dione (IIIB)

Sodium bicarbonate (16 mg), paraformaldehyde (45 mg), THF (2 ml) and triethylamine (0.1 ml) were added to 16-(methyloxalyl)androsta-1,4,9(11)-triene-3,17-dione (IIB, Example 3, reaction mixture) and on stirring for one hour at 0°, the conversion to the title compound was complete as measured by TLC. The reaction mixture was poured into pH 7 buffer and the mixture was extracted with ethyl acetate. The organic extract was washed with water, dried over sodium sulfate, filtered and the filtrate concentrated under reduced pressure to give the title compound. NMR (CDCl$_3$)=0.90, 1.44, 3.87, 5.40, 5.58, 6.03, 6.21 and 7.21 $\delta$.

EXAMPLE 5

3-Methoxy-16-methyleneandrosta-3,5,9(11)-trien-17-one (IIIAa)

3-Methoxy-16-(methyloxalyl)androsta-3,5,9(11)-trien-17-one (IIAa, Example 1, 385 mg) was refluxed with paraformaldehyde (45 mg), triethylamine (0.2 ml) and THF (4 ml) and then allowed to stand at 20°–25° for 48 hr. The reaction mixture was extracted with ethyl acetatewater, the organic layer was dried and concentrated under reduced pressure to give the title compound.

EXAMPLE 6

3-Methoxy-16-methyleneandrosta-3,5,9(11)-trien-17-one (IIIAa)

3-Methoxy-16-(methyloxalyl)androsta-3,5,9(11)-trien-17-one (IIAa, Example 1, 10 g) in THF (100 ml) and paraformaldehyde (1.17 g) and triethylamine (5.4 ml) were refluxed for 1 hr under nitrogen. The reaction mixture should be extracted, preferably with ethyl acetate/water and not methylene chloride/water which produces an emulsion. Upon workup, the title compound is obtained.

EXAMPLE 7

3-Methoxy-16-methyleneandrosta-3,5,9(11)-trien-17-one (IIIAa)

3-Methoxyandrosta-3,5,9(11)-trien-17-one (IAa, 20 g) in THF (220 ml) was combined with dimethyloxylate (11.8 g) and sodium methoxide (25%, 18.4 ml) at 0° under nitrogen. After the reactants were combined, the ice was removed. After one hour, TLC shows the reaction has gone cleanly. Triethylamine (7.0 ml), acetic acid (1.0 ml), paraformaldehyde (3 g), and methanol (28 ml) were added and the mixture stirred overnight at 20°–25°. TLC showed the reaction had gone to completion. The reaction mixture was washed with phosphate buffer (121 ml) and water (202 ml). The mixture was extracted with methylene chloride (48 ml) and again with methylene chloride (40 ml). The methylene chloride extracts were combined and back-extracted with water (80 ml) and saline (10 ml). The organic mixture was concentrated under reduced pressure to give the title compound.

EXAMPLE 8

3-Methoxy-16-methyleneandrosta-3,5-dien-17-one (IIIAa)

3-Methoxyandrosta-3,5-dien-17-one (IAa, 2.0 g) was mixed with THF (22 ml). Diethyloxylate (1.45 ml) was added and the mixture cooled in an ice bath. Sodium methoxide (25%, 1.83 ml) was added dropwise with stirring. The mixture was stirred, and after removing the ice bath for one hour TLC showed the reaction to be complete. The reaction mixture was cooled in an ice bath, acetic acid (0.1 ml) was added, followed by triethylamine (0.7 ml) and methanol (2.8 ml). Formaldehyde (37%, 0.3 g) was added and the mixture stirred for 40 min. Then formaldehyde (37% aqueous, 0.61 g) was added and the mixture stirred at 20°–25° for about 45 minutes. TLC showed the reaction to be done. Water (10 ml) and ethyl acetate (10 ml) were added and the mixture stored at about −20° overnight. The mixture was warmed, the layers are separated, and the organic layer was washed twice with saline. The aqueous layer was extracted with ethyl acetate, the ethyl acetate washed with saline, and the organic extracts combined and dried over sodium sulfate, filtered and concentrated under reduced pressure to give the title compound.

EXAMPLE 9

16-Methyleneandrosta-1,4,9(11)-triene-3,17-dione (IIIB)

Androsta-1,4,9(11)-triene-3,17-dione (IB, 0.7 g) in THF (8 ml) and dimethyloxylate (0.44 g) were combined and cooled to 3° in an ice bath. Sodium methoxide in methanol (25%, 0.685 ml) was added dropwise with no temperature rise. TLC after about ½ hr showed the reaction was nearly completed. Acetic acid (0.05 ml), triethylamine (0.26 ml) and methanol (1 ml) were added. Formaldehyde (37%, 0.28 ml) was added and the reaction mixture stirred at 20°–25°. TLC, after approximately 1½ hrs. showed the reaction was complete. The reaction mixture was added to water and extracted with ethyl acetate. The layers were separated, the aqueous layer was extracted with ethyl acetate and combined with the organic extract. The combined organic extract was washed with water and separated from the organic layer. Methylene chloride was added and the mixture dried over sodium sulfate. The mixture was filtered and the filtrate was concentrated under reduced pressure to an oil. Acetone was added and the title compound was obtained upon crystallization, m.p. 157°–160°.

EXAMPLE 10

16-Methyleneandrosta-1,4,9(11)-triene-3,17-dione (IIIB)

Sodium methoxide in methanol (25%, 6.85 ml) is added dropwise to a mixture of androst-1,4,9(11)-triene-3,17-dione (IB, 7.05 g) in THF (80 ml) and methylene chloride (8 ml) containing dimethyloxalate (4.38 g) previously cooled to 4°. After one hour at 4°, the preparation of the 16-oxalate salt is complete and the following reagents were added sequentially: acetic acid (0.5 ml), triethylamine (2.6 ml), methanol (10 ml), and aqueous formaline (37%, 2.8 ml). The reaction mixture was warmed to 20°–25° and after one hour the reaction was complete. The reaction mixture was poured into water and extracted twice with ethyl acetate. The ethyl acetate extracts were combined, washed with water, dried over sodium sulfate, and concentrated under reduced pressure to a solid. The solid was dissolved in methylene chloride (2.5 ml), following which the methylene chloride was evaporated. The solid was again dissolved in dry THF (25 ml), following which the THF was evaporated. The solid was then dissolved in dry THF (50 ml) for use in the following reaction.

EXAMPLE 11

6-Methyl-16-methyleneandrosta-4,6-diene-3,17-dione (IIIA)

6-Methylandrosta-4,6-diene-3,17-dione (IA, U.S. Pat. No. 3,177,966, Example 16, 3.0 g) was dissolved in THF (32 ml) and dimethyloxalate (1.64 g) was added. The mixture was cooled under nitrogen to 0°. Sodium methoxide in methanol (25%, 2.75 ml) was added dropwise. The mixture was stirred approximately 2 hrs. at 0°; then neutralized with acetic acid (0.12 ml). Triethylamine (1.2 ml) and methanol (5.0 ml) were added followed by formaldehyde solution (37%, 1.13 ml). Following addition of all the reactants, the ice bath was removed and the reaction stirred at 20°–25° for 1.5 hrs. Water (50 ml) was added, followed by ethyl acetate and methyl t-butyl ether. These phases were separated and the organic phase was washed twice with saline. The combined aqueous layers were back extracted once with ethyl acetate and the combined organic extracts were dried over sodium sulfate after the addition of some methylene chloride. The mixture was filtered through Celite and the filtrate removed under reduced pressure to give an oil which was chromatographed over silica gel (230-400 mesh, 140 g). The appropriate fractions were pooled and concentrated to give the title compound.

EXAMPLE 12

17α-Ethinyl-17β-hydroxy-16-methyleneneandrost-4,9(11)-dien-3-one (IVA)

Acetylene was added to THF (600 ml) at −70° through a gas sparger for ½ hr. Butyl lithium (1.6N, 156 ml) was added dropwise to the acetylene mixture. A solution of 3-methoxy-16-methyleneandrost-3,5,9(11)-trien-17-one (IIIAa, Example 2, 82.96 mM) in 200 ml of THF was cooled to −40° and 500 ml of the above lithiated acetylene solution was added to the steroid solution over a period of 10 minutes maintaining a temperature at −30° to −40°. An additional 100 ml of acetylide solution was added over the next 20 minutes, at which time 2.5 equivalents had been added, and the reaction was complete. The reaction mixture was poured into a phosphate buffer (10%, 550 ml). The mixture was concentrated to 600 ml and extracted with methylene chloride (twice with 100 ml and twice with 50 ml). The combined organic extracts were treated with 20 ml of 6N hydrochloric acid in 100 ml of water with vigorous stirring under nitrogen. When hydrolysis of the 3-enol ether was complete as measured by TLC, the aqueous phase was separated, the organic layer washed with 100 ml of water, dried over sodium sulfate and concentrated to a solid. The solid was triturated in methanol and the title compound isolated in three crops, m.p. 216°–217°; NMR (CDCl$_3$) 0.78, 1.32, 2.57, 5.07, 5.36, 5.60 and 5.72 δ.

EXAMPLE 13

17α-Acetyl-17β-hydroxy-16-methyleneandrost-4,9(11)-dien-3-one (VA)

The mercuric oxide (red, 1.2 g), which had been dissolved in concentrated sulfuric acid (1.6 ml) and water (25 ml) was added to a solution of 17α-ethinyl-17β-hydroxy-16-methyleneandrosta-4,9(11)-dien-3-one (IVA, Example 11, 10 g) in methanol (600 ml) and THF (125 ml). The reaction mixture was stirred overnight at 20°–25° at which time the reaction was complete as measured by TLC. The solids were removed by filtration through a Celite pad. The filtrate was concentrated under reduced pressure to a solid which was triturated with methanol (25 ml). The mixture was filtered and the solids dried to give the title compound, m.p. 147°–162°; NMR (CDCl$_3$) 0.88, 1.35, 2.35, 5.02, 5.50 and 5.75 δ.

EXAMPLE 14

16-(Phenylsulfinylmethyl)pregn-4,9(11),16-triene-3,20-dione (VIA)

A solution of phenylsulfinylchloride (2.5N, 1.4 ml) in methylene chloride was added dropwise over a period of 1.5 hrs to a solution of 17-acetyl-17β-hydroxy-16-methyleneandrost-4,9(11)-dien-3-one (VA, Example 12, 1 g) in methylene chloride (10 ml) containing triethylamine (0.82 ml) previously cooled equal to 31 55°. Water was added to the reaction mixture, the organic phase separated, washed with water, dried over sodium sulfate, and concentrated under reduced pressure to a partially crystalline substance. Crystallization from toluene gives the title compound, m.p. 160°–163°; NMR (CDCl$_3$) 0.87, 1.36, 2.11, 4.03, 5.50 and 5.75 δ.

EXAMPLE 15

17α-Hydroxy-16-methylenepregna-4,9(11)-diene-3,20-dione (VIIA)

A mixture of 16-(phenylsulfinylmethyl)pregn-4,9(11),16-triene-3,20-dione (VIA, Example 14, 100 mg) in toluene (1 ml) and methanol (0.14 ml) containing 53 μl of trimethylphosphite was heated for 16 hrs at 65° in a sealed vial. TLC showed the reaction to be complete. Methylene chloride was added, the reaction mixture washed with water, the organic phase separated, dried and concentrated under reduced pressure to give the title compound. NMR (CDCl$_3$) 0.77, 1.35, 2.31, 5.10, 5.27, 5.57 and 5.75 δ.

EXAMPLE 16

17α-Ethinyl-17β-hydroxy-16-methyleneandrost-1,4,9(11)-trien-3-one (IVB)

Acetylene gas was sparged to dry THF (166 ml) at 20°–25° for ½ hr to saturate the solution. The acetylene/THF solution was cooled to −70° and butyllithium (1.55N, 32.25 ml in hexane) was added dropwise over 20 min to give a clear solution of lithium acetylide. 50 ml of the lithium acetylide solution was placed in a separate flask at −70°. 16-methyleneandrost-1,4,9(11)-trien-3,17-dione (IIIB, Example 10) in THF (50 ml) was added dropwise over 35 min to the remainder of the lithium acetylide. An additional 25 ml of the retained lithium acetylide solution was added and after ½ hr at −70° the reaction was quenched into 400 ml of phosphate buffer. The product was extracted into ethyl acetate/methylene chloride, the phases separated, the organic phase dried over sodium sulfate, and concentrated under reduced pressure to give a solid which was crystallized from ethyl acetate to give the title compound, m.p. 234°–237°; NMR (CDCl$_3$) 0.83, 1.43, 2.47, 2.47, 5.12, 5.42, 5.65, 6.10, 6.32 and 7.22 δ.

EXAMPLE 17

17α-Acetyl-17β-hydroxy-16-methyleneandrost-1,4,9(11)-trien-3-one (VB)

Mercuric oxide (0.4 g) in concentrated sulfuric acid (0.53 ml) in water (8.3 ml) was added to a solution of 17α-ethinyl-17β-hydroxy-16-methyleneandrosta-1,4,9(11)-trien-3-one (IVB, Example 16, 3.2 g) in methanol (100 ml) and THF (21 ml). The reaction mixture was stirred 5.5 hrs at 20°–25°. Sodium carbonate (1N, 20 ml) and ethyl acetate (50 ml) are added. The mixture is filtered through celite. The filtrate was concentrated under reduced pressure. The product was extracted from the aqueous phase by use of ethyl acetate/methylene chloride. The ethyl acetate/methylene chloride extract is dried over sodium sulfate and concentrated to a solid which is recrystallized from methanol to give the title compound, m.p. 185°–190°; NMR (CDCl$_3$ 0.91, 1.42, 2.23, 5.20, 5.56, 6.10, 6.27 and 7.23 δ.

EXAMPLE 18

16-(Phenylsulfinylmethyl)pregn-1,4,9(11),16-tetraene-3,20-dione (VIB)

Phenylsulfinyl chloride in methylene chloride (2.5N, 2.4 ml) was added to a mixture of 17α-acetyl-17β-hydroxy-16-methyleneandrost-1,4,9(11)-trien-3-one (VB, Example 17, 1 g) in methylene chloride (10 ml) and triethylamine (0.82 ml) previously cooled to −30° over a period of 2 hrs. The reaction is plunged into phosphate buffer (pH 7, 10 ml); the phases are separated; the aqueous phase is extracted with methylene chloride; the organic phases are combined and dried over sodium sulfate and concentrated under reduced pressure to an isomeric mixture of the title compound. The isomers are separated by chromatography on silica gel (50 g), eluting with acetone/hexane: 5/95 to give the title compound, NMR (CDCl$_3$) 0.89, 1.42, 2.10, 4.03, 5.5, 6.0, 6.27, 7.20 $\delta$.

EXAMPLE 19

17$\alpha$-Hydroxy-16-methylenepregn-1,4,9(11)-triene-3,20-dione (VIIB)

Trimethylphosphite (0.3 ml) and triethylamine (0.3 ml) are added to a solution of 16(phenylsulfinylmethyl)-pregn-1,4,9(11),15-tetraene-3,20-dione (VIB, Example 18, 538 mg of the mixed isomers) in toluene (5 ml) and methanol (0.7 ml). The mixture was heated at 85° in a sealed vial until the reaction was complete. The reaction mixture was poured into a buffer solution and extracted with ethyl acetate. The ethyl acetate extract was washed with water, dried over sodium sulfate, and concentrated to a solid which is recrystallized from ethyl acetate to give the title compound. NMR (CDCl$_3$) 0.70, 1.36, 2.26, 5.10, 5.51, 6.00, 6.20 and 7.17 $\delta$.

EXAMPLE 20

17$\alpha$-Ethynyl-17$\beta$-hydroxy-6-methyl-16-methyleneandrosta-4,6-dien-3-one (IVA)

Acetylene saturated THF (45 ml, 4.2 equivalents) was cooled to −72° over 5 min while addition of acetylene continued. The acetylene bubbling was stopped and n-butyl lithium (1.55M, 16.6 ml, 4.0 equivalents) was added over 15 min keeping the temperature less than −65°, mostly at −68°. The mixture was cooled to −90° and added to 6-methyl-16-methyleneandrosta-4,6-diene-3,17-dione. (IIIA, Example 11, 2.0 g) in THF (10 ml) previously cooled to −105° via an insulated teflon canula over about 3 min. The mixture was exothermically warmed to −87° and was recooled to −90° (bath at −93°). After 3.5 hr TLC indicated the reaction was complete. Acetic acid (1.84 ml, 5 equivalents) was added in methanol (10 ml) previously cooled to −98°. The mixture was warmed to 20°-25° and phosphate buffer (20 ml) and ethyl acetate (20 ml) were added. The layers were separated. The organic layer was washed with buffer/saline (1/1). The aqueous layer was back extracted with ethyl acetate which was washed with saline. The organic extracts were combined, dried over sodium sulfate, filtered and concentrated under reduced pressure to an oil. Ethyl acetate was added along with a seed crystal and the mixture sat over night at 20°-25°, and then −20° for 4 hr. The crystals were obtained by filtration, washed with ethyl acetate/hexane: (1/1) to give the title compound.

EXAMPLE 21

17$\alpha$-Acetyl-17$\beta$-hydroxy-6-methyl-16-methyleneandrosta-4,6-dien-3-one (VA)

Mercuric oxide (83 mg) dissolved in water (18 ml) containing sulfuric acid (0.11 ml) was added to 17$\alpha$-ethynyl-17$\beta$-hydroxy-6-methyl-16-methyleneandrosta-4,6-dien-3-one (IVA, Example 20, 1.30 g) dissolved in a methanol (19 ml)-THF (3.8 ml) mixture. The mixture was heated at 40° (bath temperature) for 6 hr and then permitted to sit at 20°-25° overnight. Celite (1.7 g) and phosphate buffer (2 ml) were added, the mixture stirred and filtered. The solids were washed with methanol and THF. The filtrate was concentrated under reduced pressure until solids dropped out. Methanol was added and the mixture heated, seeded. The mixture was concentrated under reduced pressure, methylene chloride was added, the mixture was washed with buffer, dried over sodium sulfate, filtered. The filtrate was concentrated under reduced pressure to give the title compound.

EXAMPLE 22

6-Methyl-16-(phenylsulfinylmethyl)pregna-4,6,16-triene-3,20-dione (VIA)

17$\alpha$-Acetyl-17$\beta$-hydroxy-6-methyl-16-methyleneandrosta-4,6-dien-3-one (VA, Example 21, 200 mg) was mixed with methylene chloride (2.0 ml) and stored overnight at −20°. The steroid mixture was then cooled to −37° under nitrogen. Trimethylamine (29 ml) as a gas was added directly to the steroid mixture over about 10 min. Phenyl sulfenyl chloride (2.5M in methylene chloride, 0.45 ml, 2 equivalents) is added at −40° over a period of 1.3 hr. TLC shows the reaction is approximately 98% complete. Hydrochloric acid (10%, 3 ml) is added and the mixture warmed to 20°-25°. The layers are separated and the aqueous layer is back extracted. The organic layers are combined, washed with phosphate buffer (10%) and the buffer is back extracted. The organic phases are combined, dried over sodium sulfate, filtered and concentrated under reduced pressure. The product was purified on a 20×20 silica gel plate eluting with acetone/methylene chloride (10/90) to give the title compound.

EXAMPLE 23

17$\alpha$-Hydroxy-6-methyl-16-methylenepregna-4,6-diene-3,20-dione (VIIA')

6-Methyl-16-(phenylsulfenylmethyl)-pregna-4,6-diene-3,20-dione (VIA, Example 22, 150 mg), toluene (1.25 ml), methanol (0.216 ml), triethylamine (0.011 ml) and finally trimethylphosphite (0.076 ml) were added to a vial which was sealed, stirred and heated at 100° for 4.75 hr. The mixture was concentrated under reduced pressure to an oil which is TLC'd on silica gel eluting with acetone/methylene chloride (5/95) to give the title compound.

EXAMPLE 24

17$\alpha$-Hydroxy-6-methyl-16-methylenepregna-4,6-diene-3,20-dione 17-acetate (VIII)

Using the procedure of U.S. Pat. No. 4,154,748, Example 12, 17$\alpha$-hydroxy-6-methyl-16-methylenepregna-4,6-diene-3,20-dione (VIIA', Example 23), is converted to the title compound.

EXAMPLE 25

3-Methoxy-16-methyleneandrosta-3,5-dien-17-one (IIIAa)

3-Methoxyandrosta-3,5-dien-17-one (I, 50.0 g) was dissolved in THF containing TEA (1 ml). Dimethyloxalate (55.5 ml) was added and the mixture cooled to 2°. Sodium methoxide (25%) in methanol (45.7 ml) was added slowly over 10 minutes. The ice bath was removed and the reaction warmed to 24° over five minutes with stirring. The mixture was stirred at 20°-25° for 55 minutes, then cooled to 5° over 10 minutes. Acetic acid (2.4 ml) was added, immediately followed by TEA (17.4 ml), then paraformaldehyde (7.49 g), followed by methanol (63 ml). The ice bath was removed and the mixture warmed to 20°–25° over 5 minutes. The mixture was stirred at 28° for 5 hrs and stored in a freezer (−20°) overnight. The mixture was then warmed to 20°–25° and stirred at 25° for 4 hrs for a total time of approximately 9.0 hrs at 20°–28°. Water (300 ml) and ethyl acetate (300 ml) were added, the mixture stirred and the layers separated. The organic layer was washed with saline (2×100 ml). The aqueous portion is backextracted with ethyl acetate (2×100 ml, washing each with 50 ml of saline). The organic phases are combined, concentrated under reduced pressure to an oil, taken up in methylene chloride (450 ml) and ethyl acetate (200 ml). This mixture was dried over sodium sulfate, filtered and concentrated under reduced pressure to a solid. Trituration of the solid with boiling methanol (100 ml) containing 1% TEA gives the title compound in crystalline form.

EXAMPLE 26

17α-Ethinyl-17β-hydroxy-3-methoxy-16-methyleneandrosta-3,5-diene (IVAa)

Acetylene was bubbled through THF (450 ml) for 45 min at 20°–25°. The mixture was cooled to −70° over 15 min while acetylene saturation was continued. N-butyllithium (1.6M, 150 ml) was added dropwise over about 45 min, maintaining the temperature at ≦−68°. The mixture was then warmed to −35° over 30 min. 3-Methoxy-16-methyleneandrosta-3,5-dien-17-one (IIIAa, Example 25, 30 g) in THF (150 ml) was added dropwise over 15 min, maintaining the temperature at about −25°. The mixture was stirred for 10 min; then the solution was added slowly to phosphate buffer (1N, 800 ml) plus ice water (300 ml) at 0°. The transfer took approximately 1 hr, following which the mixture was stirred. Ethyl acetate (500 ml) was added and the layers separated. The ethyl acetate layer was washed with saline (2×300 ml). The aqueous phase was back-extracted with ethyl acetate (2×300 ml). The ethyl acetate back extracts were combined and washed once with saline (200 ml). The organic phases were combined, dried over anhydrous sodium sulfate, filtered and concentrated under reduced pressure to a solid. The solid was triturated with hot methanol (100 ml) for 10 min, cooled to 20°–25°, then cooled to −20° for 2 hrs. The mixture was filtered, the crystals washed with cold methanol containing TEA, and dried under reduced pressure to give the title compound.

EXAMPLE 27

17α-Ethinyl-17β-hydroxy-6β-(N-phenyl-N-ethylaminomethyl)-16-methyleneandrosta-4-en-3-one 17α-Ethinyl-17β-hydroxy-3-methoxy-16-methyleneandrosta-3,5-diene (IVAa, Example 26, 5 g), ethyl aniline (2.05 ml), THF (37.5 ml), and formaldehyde (37%, 1.33 g) were mixed. p-TSA (140 mg) was added and the mixture stirred overnight at 20°–25°. TLC showed the reaction to be complete. Water (100 ml) was added, the mixture filtered, the solids washed twice with water/THF; 2/1, the solid material was dried under nitrogen for 5 hours to give the title compound. NMR (CDCl$_3$) 0.85, 1.31, 2.52, 5.23, 5.82, 6.7 and 7.2δ.

EXAMPLE 28

17α-Ethinyl-17β-hydroxy-6,16-dimethyleneandrosta-4-en-3-one (IVA)

17α-Ethinyl-17β-hydroxy-6β-(N-phenyl-N-ethylaminomethyl)-16-methyleneandrosta-4-en-3-one (Example 27) in THF (20 ml) are mixed. Degassed hydrochloric acid (6N, 55 ml plus 20 ml THF) are added. The mixture is stirred overnight at 20°–25° under nitrogen, at which time TLC shows the reaction to be complete. Water (110 ml) is added, the mixture filtered, the solids washed with 10% hydrochloric acid, twice with water, once with 5% sodium bicarbonate, and three times with water to neutrality. Solids were then dried under nitrogen overnight to give the title compound.

EXAMPLE 29

17α-Acetyl-17β-hydroxy-6,16-dimethyleneandrosta-4-en-3-one (VA)

Mercuric oxide red (0.32 g) was mixed with sulfuric acid/water (sulfuric acid, 0.4 ml; water, 6.0 ml) and let stand overnight. 17α-Ethinyl-17β-hydroxy-6,16-dimethyleneandrosta-4-en-3-one (IVA, Example 28, 5.0 g) is mixed with THF (15 ml). The mercuric sulfate solution is added and the reaction heated to 41°–49° over a period of 6 hrs at which time TLC indicates the reaction is completed. Sodium carbonate (0.79 g) in water (10 ml) is added and the mixture stirred for 5 min. Celite (5 g) is added and the mixture stirred ½ hr at 20°–25°. The mixture is filtered through Celite (5 g), the solids washed with methanol/THF; 1/1 (2×10 ml) and once with THF (10 ml), followed by methylene chloride (10 ml). The filtrate and washings are concentrated under reduced pressure to about 35 ml, at which point crystals begin forming. Methanol (50 ml) is added and the mixture again concentrated under reduced pressure and permitted to sit overnight at 20°–25° under nitrogen atmosphere. Water (500 ml) is added, slowly at first, with stirring over a period of 15 min. The mixture is filtered, the solids washed with water (3×20 ml), and hexane (2×10 ml). The solids were dried under nitrogen to give the title compound.

EXAMPLE 30

6-Methylene-16-(phenylsulfinylmethyl)pregna-4,16-diene-3,20-dione (VIA)

17α-Acetyl-17β-hydroxy-6,16-dimethyleneandrosta-4-en-3-one (VA, Example 29, 8.0 g) is dissolved in methylene chloride (66 ml) and cooled to −20°. Trimethylamine (2.56 ml) at −20° and methylene chloride (5 ml) are mixed and the trimethylamine mixture transferred by syringe to the steroid solution. To the cold steroid solution was added phenylsulfonylchloride (1.0 equivalent) by a syringe pump over 1 hr. TLC shows the reaction approximately 80–85% complete. Phenylsulfonylchloride (0.25 equivalent) was added over approximately 10 min, TLC showing the reaction to be approximately 95% complete. Phenylsulfonylchloride (0.10 equivalent) was then added for a total of 1.35 equivalence, at which time TLC shows the reaction to be complete. Hydrochloric acid (10%, 40 ml) was added all at once, the temperature now being 7°, and the mixture stirred for about 10 min. The phases are separated. The aqueous portion is back extracted with methylene chloride (10 ml). The organic extracts are washed with phosphate buffer (25 ml) and back extracted with methylene chloride (10 ml). The organic extracts are combined, dried over sodium sulfate overnight at 20°–25°. This mixture is filtered and the filtrate concentrated under reduced pressure to an oil, which is the title compound.

EXAMPLE 31

17α-Hydroxy-6,16-dimethylenepregna-4-ene-3,20-dione (VIIA″)

6-Methylene-16-phenylsulfonylmethylpregna-4,16-diene-3,20-dione (VIA, Example 30, 2.0 g) is placed in a 30-ml vial under nitrogen. Toluene (20 ml), methanol (2.89 ml), TEA (0.181 ml) and trimethylphosphite 1.02 ml) are added. After 1 hr at 20°–25°, the sealed vial was plunged into a hot oil bath with a bath temperature of 90° which is stirred at 90° for 4 hrs, at which time TLC shows the reaction to be essentially complete. The reaction mixture is transferred to a separatory funnel and water (10 ml) is added. Ethyl acetate (10 ml) is added to the organic mixture, which is washed with water (2×10 ml). The aqueous portion is back extracted with toluene/ethyl acetate: 1/1. After the phases are separated, the organic phase is filtered through sodium sulfate and the filtrate is concentrated under reduced pressure to a volume of about 8 ml. This concentrate is permitted to sit at 20°–25° for approximately ½ hr. The resulting crystals are washed down into a flask with toluene (2 ml) and cooled to 5° for 2 hrs, then to −20° for 48 hrs. The crystals were collected with toluene (−20°), then with hexane three times and dried under nitrogen to yield the title compound.

EXAMPLE 32

17α-Hydroxy-6-methyl-16-methylenepregna-4,6-diene-3,20-dione 17-acetate (VIII)

17α-Hydroxy-6,16-dimethylenepregna-4-ene-3,20-dione (VIIA″, Example 31, 50 mg) is slurried in toluene (1.5 ml). Acetic anhydride (95 μl, 7 equivalents) and p-TSA/water (8 mg, 0.3 equivalents) are added. The reaction vessel is capped and heated at 85° for 3 hrs 20 min, then pulled from the heat, cooled and TLC shows the reaction is approximately 70% complete. The reaction mixture is heated for an additional 3 hrs, permitted to stand at 20°–25° overnight, at which time TLC shows the reaction is complete. Hydrochloric acid (6N, 200 μl) is added and the mixture stirred 1 hr at 20°–25°. On work-up, the title compound is obtained.

EXAMPLE 33

17α-Ethynyl-17β-hydroxy-3-methoxy-16-methyleneandrosta-3,5-diene (IVAa)

THF (400 ml) was cooled to −40°. Acetylene was sparged thru the THF, the temperature until rising to −28° and then over 0.5 hr dropping to −36°. Acetylene bubbling was continued another 0.5 hr. The mixture was cooled to −43° and acetylene bubbled for an additional 0.5 hr. 3-Methoxy-16-methyleneandrosta-3,5-dien-17-one (IIIAa, Example 8, 40.0 g) was added with stirring maintaining the −50° cooling bath.

Diisopropylamine (44 ml) and THF (50 ml) were mixed and cooled to 8°. n-Butyl lithium (1.6M in hexane, 194 ml) was added at such a rate as to keep the exotherm below 25°. When the addition was complete, the lithium diisopropylamide mixture was transferred via a canula to an addition funnel and then added dropwise to the steroidacetylene mixture while maintaining the reaction temperature < −38° (bath temperature was −50°). When addition was complete (65 minutes) TLC indicated the reaction was approximately 98% complete. The reaction mixture was dumped slowly into saline/water (1 l, 1/1) and stirred. The layers were separated. The aqueous layer was extracted with ethyl acetate (200 ml). The organic phases were combined, washed with saline, dried over sodium sulfate after addition of triethylamine (1 ml) and concentrated under reduced pressure to a volume of about 80 ml. Methanol (200 ml) and triethylamine (1 ml) were added and the mixture concentrated under reduced pressue to about 100 ml. Methanol (200 ml) was added and the mixture again concentrated to about 100 ml. The mixture was filtered, the solids washed with cold methanol to give the title compound.

EXAMPLE 34

17α,21-Dihydroxy-16-methylenepregna-4,9(11)-diene-3,20-dione 21-acetate (IXA)

17α-Hydroxy-16-methylenepregna-4,9(11)-diene-3,20-dione (VIIA, Example 15, 400 mg) is dissolved in THF (3 ml having a peroxide content equivalent to 0.01 g of iodine per ml of THF) and methanol (1.8 ml) with stirring. Calcium oxide (600 mg finely powdered) is added followed by iodine (600 mg). When the reaction is complete, about 3 hrs, methylene chloride is added, the mixture filtered, the filtrate washed successively with aqueous sodium iodide solution, sodium thiosulfate solution, water, dried, and concentrated under reduced pressure without applying any heat. The 21-iodo intermediate is dissolved in dry acetone (10 ml) and heated under reflux for 18 hrs with anhydrous potassium acetate (1.0 g). Water is added and the product is extracted with methylene chloride. The methylene chloride extract is washed with water, dried and concentrated under reduced pressure to give the title compound.

EXAMPLE 35

17α,21-Dihydroxy-16-methylenepregna-1,4,9(11)-triene-3,20-dione 21-acetate (IXB)

Following the general procedure of Example 34 and making noncritical variations but starting with 17α-hydroxy-16-methylenepregna-1,4,9(11)-triene-3,20-dione (VIIB, Example 19), the title compound is obtained.

EXAMPLE 36

17α-Ethinyl-17β-hydroxy-16-methyleneandrost-4-en-3-one (IVA)

Triethylamine (0.63 mole) is added to dry THF (100 ml) at −20° under a nitrogen atmosphere. This is followed by addition of n-butyl lithium (1.6N in hexane, 0.62 mole). The cold solution is added to an acetylene-saturated THF solution (500 ml dry THF saturated at −10° with 1.1 mole acetylene, then cooled to −20°). 3-Methoxy-16-methyleneandrosta-3,5-dien-17-one (IIIAa, Example 8, 0.32 mmoles) in dry THF (100 ml) is added to the monolithium acetalide solution while maintaining the temperature at −20°. Hydrolysis of the reaction mixture performed by adding hydrochloric acid (6N, 300 ml) and mixing for 1.5 hour at 30°. Methanol and water are added, the precipitate isolated to give the title compound. NMR (CDCl$_3$) 0.83, 1.20, 2.52, 5.07, 5.35 and 5.68 δ

EXAMPLE 37

17α-Acetyl-17β-hydroxy-16-methyleneandrost-4-en-3-one (VA)

A mixture of mercuric oxide (4.6 mmole) dissolved in sulfuric acid (1.3M, 38 ml) is added to a slurry of 17α-ethinyl-17β-hydroxy-16-methyleneandrost-4-en-3-one (IVA, Example 36, 30.0 g) in acetone (300 ml) under a nitrogen atmosphere. The mixture is heated at 50° overnight and then cooled to 20°–25°. The mixture is neutralized with sodium bicarbonate, filtered through celite. Acetone and water are added. Upon workup a crude product is obtained. This crude product purified by stirring in a 2% acetic acid-methylene chloride mixture (0.3 g/ml) with zinc dust (5%) for 2–3 hours at 25°. The mixture is filtered through magnesium silicate, then concentrated to solid. The crude material is crystallized from acetone to give the title compound. NMR ($CDCl_3$) 0.93, 1.20, 2.26, 3.2, 5.12 and 5.70 δ

EXAMPLE 38

16-(Phenylsulfinylmethyl)pregna-4,16-diene-3,20-dione (VIA)

Trimethylamine (0.39 mole) is added to a −20° mixture of 17α-acetyl-17β-hydroxy-17-methyleneandrost-4-en-3-one (VA, Example 37, 45.0 g) in dry methylene chloride (450 ml) under a nitrogen atmosphere. A solution of phenylsulfenyl chloride in methylene chloride (2M, 0.18 mole) is then added dropwise over 0.5 hours while maintaining the temperature at −20°. After an additional 20 minutes at −20° the mixture is quenched with methanol (4.5 ml) then with hydrochloric acid (10% v/v). Upon aqueous workup, drying over sodium sulfate, removal of the solvent gives the title compound which is used without further purification in the next step. NMR ($CDCl_3$) 0.96, 1.02, 1.20, 2.08, 2.18, 3.9, 5.7 and 7.5 δ

EXAMPLE 39

17α-Hydroxy-16-methylenepregna-4-ene-3,20-dione (VIIA)

The crude 16-(phenylsulfinylmethyl)pregna-4,16-diene-3,20-dione (VIA, Example 38) is slurried in toluene (300 ml) under a nitrogen atmosphere. Methanol (2 mmole), triethylamine (0.13 mmole) and then trimethylphosphite (0.79 mmole) are added. The reaction mixture is sealed and heated under pressure at 90° for 4 hours, then cooled to 20°–25°. The reaction mixture is subjected to acid hydrolysis of the access trimethylphosphite, base and buffer washes and finally crystallization from toluene/heptane to give the title compound. NMR ($CDCl_3$) 0.82, 1.20, 1.30, 3.5, 5.04, 5.21 and 5.68 δ

EXAMPLE 40

17α-Hydroxy-3β-methoxy-16-methylenepregna-3,5-diene-20-one (VIIAa)

Trimethylorthoformate (180 mmole) and pyridine hydrochloride (8.7 mmole) are added to a mixture of 17α-hydroxy-16-methylenepregn-4-ene-3,20-dione (VIIA, Example 39, 30.0 g) in a 1:1 ethyl acetate/methanol mixture under a nitrogen atmosphere. The slurry is heated at 40° for 2 hours. The solvent is changed to ethyl acetate and heating is continued at 50° for 1 hour. Triethylamine (16 mmole) is added followed by hexane (30 ml). The slurry is cooled and filtered to give the title compound. NMR ($CDCl_3$) 0.83, 0.98, 2.28, 3.2, 3.52, 5.1 and 5.2 δ

EXAMPLE 41

17α-Hydroxy-6,16-dimethylenepregn-4-ene-3,20-dione (VIIA″)

To a mixture of 17α-hydroxy-3β-methoxy-16-methylenepregna-3,5-dien-3-one (VIIAa, Example 40, 2.5 g) in N-ethylaniline (8 mmole) and THF (12 ml) under nitrogen atmosphere is added 37% aqueous formaldehyde (8 mmole) and oxalic acid (0.7 mmole). The mixture is stirred at 20°–25° overnight at which time the solvent is removed under reduced pressure and replaced with methylene chloride (25 ml). After an aqueous workup, the organic layer is stirred under nitrogen with degassed hydrochloric acid (6N, 25 ml) in a sealed vessel at 40° for 5 hours. Aqueous workup neutralization and crystallization from ethyl acetate gives the title compound. NMR ($CDCl_3$) 0.83, 1.10, 2.31, 3.3, 4.90, 5.02, 5.23 and 5.85 δ

EXAMPLE 42

17α-Hydroxy-6-methyl-16-methylenepregna-4,6-diene-3,20-dione 17-acetate (VIII)

17α-Hydroxy-6,16-dimethylenepregn-4-ene-3,20-dione (VIIA″, Example 41, 0.5 g) was slurried in toluene (14 ml) under a nitrogen atmosphere. Acetic anhydride (0.95 ml) was added followed by p-TSA (80 mg). The mixture is heated in a sealed vial at 85° for 6.5 hr at which time TLC indicated the reaction was complete. The mixture was concentrated under reduced pressure to an oil. Methanol (about 10 ml) was added followed by hydrochloric acid (10%, 1.5 ml) and the mixture stirred under nitrogen for 1 hr. Water was added, the mixture filtered. The solid was washed with bicarbonate, distilled water and dried overnight under nitrogen to give the title compound (515 mg, 92% chemical yield).

CHART A

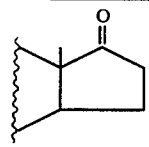

(I)

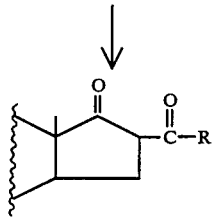

(II)

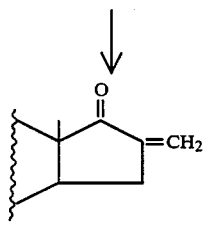

(III)

CHART B
(A) 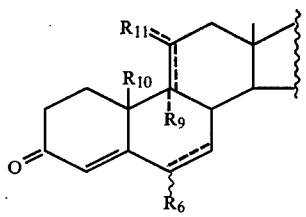
(B) 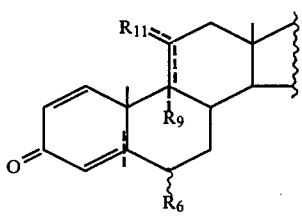
(C) 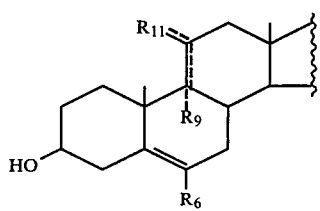
CHART C
(Aa) 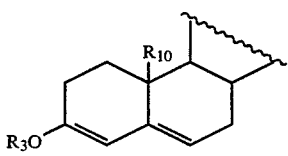
(Ab) 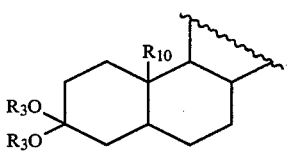
(Ac) 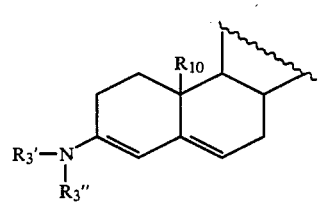
(Ca) 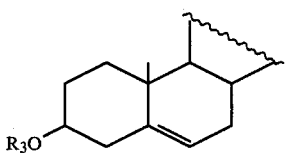
-continued
CHART C
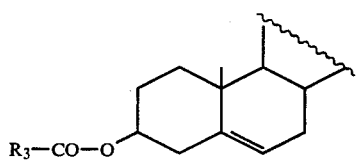 (Cb)
CHART D
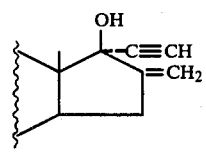 (IV)
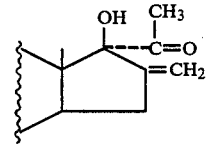 (V)
$R_{22}$—S—M (XII)
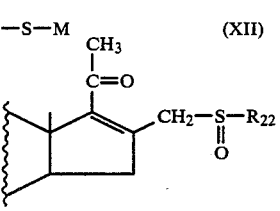 (VI)
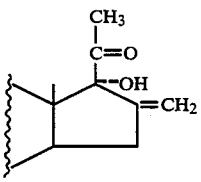 (VII)
CHART E
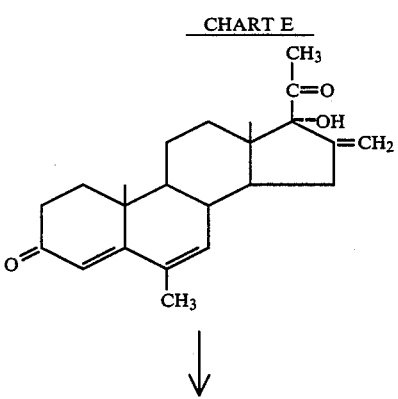 (VIIA')

CHART E

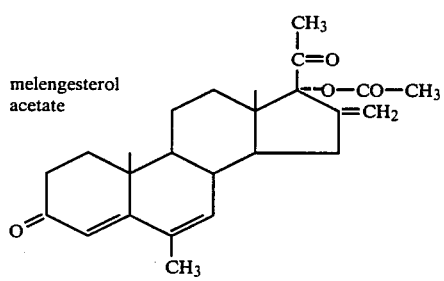
melengesterol acetate

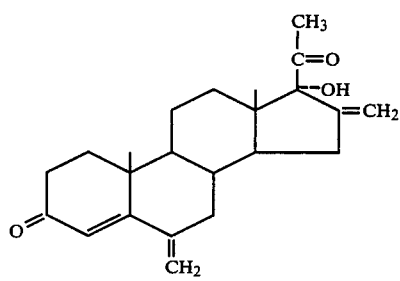
(VIIA")

CHART F

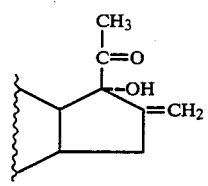
(VII)

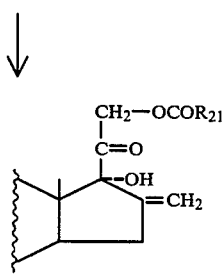
(IX)

16-methylene corticoid

16β-methyl corticoid

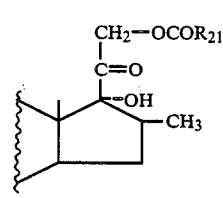
(X)

-continued
CHART F

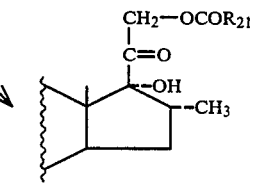
(VIII) 16α-methyl corticoid (XI)

I claim:

1. A 17β-hydroxy steroid selected from the group consisting of

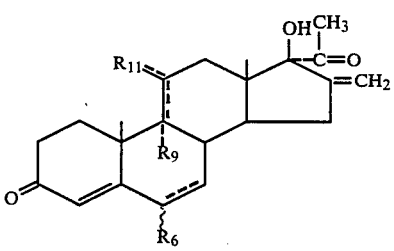
(VAA)

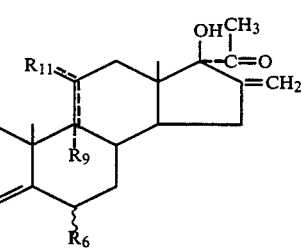
(VB)

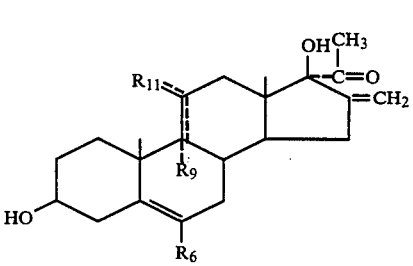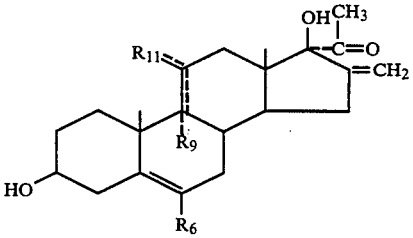
(VC)

and $C_3$ protected forms thereof where $R_6$ is a hydrogen or fluorine atom, methyl or methylene group, when $R_6$ is methylene, there are no 6–7 double bonds in formula (A) or 5–6 double bonds in formula (C);

$R_9$ is nothing or a hydrogen or fluorine atom, which includes the Δ9(11) and 9β,11β-epoxide functionality;

$R_{11}$ is nothing or a hydrogen or oxygen atom, an α-hydroxy group, or a β-hydroxy group, which includes the Δ9(11) and 9β,11β-epoxide functionality;

∼ indicates that the attached atom or group can be in either the α or β configuration; and ___ is a single or double bond.

2. A 17β-hydroxy steroid according to claim 1 of the formula

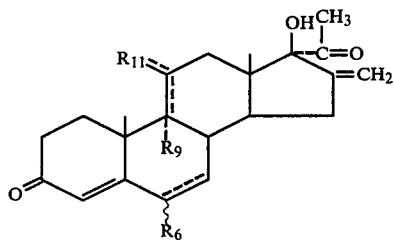 (VAA)

and C$_3$ protected forms thereof where R$_6$, R$_9$, R$_{11}$, $\sim$ and .... are defined in claim 1.

3. A 17$\beta$-hydroxy steroid according to claim 2 where the C$_3$ protecting group is selected from the group consisting of enol ethers, ketals or enamines of the formula

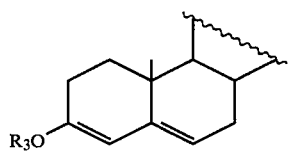 (Aa')

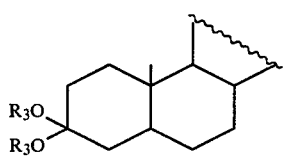 (Ab')

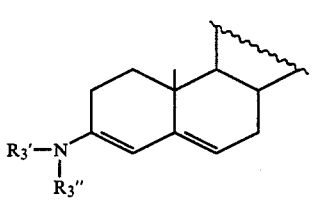 (Ac')

where
R$_3$ is alkyl of 1 thru 5 carbon atoms with the proviso that with the ketal (c), the R$_3$ groups can be connected;
R$_3'$ is alkyl of 1 thru 5 carbon atoms; and
R$_3''$ is alkyl of 1 thru 5 carbon atoms.

4. A 17$\beta$-hydroxy steroid according to claim 3 where the C$_3$ protecting group is selected from the group consisting of methyl enol ether, ethyl enol ether, ethylene ketal, and pyrolidine enamine.

5. A 17$\beta$-hydroxy steroid according to claim 2 where R$_{10}$ is a methyl group.

6. A 17$\beta$-hydroxy steroid according to claim 2 where R$_6$ is a hydrogen atom, methyl or methylene group.

7. A 17$\beta$-hydroxy steroid according to claim 6 which is 17$\alpha$-acetyl-17$\beta$-hydroxy-16-methyleneandrosta-4,9(11)-dien-3-one.

8. A 17$\beta$-hydroxy steroid according to claim 16 which is 17$\alpha$-acetyl-17$\beta$-hydroxy-6-methyl-16-methyleneandrosta-4,6-dien-3-one.

9. A 17$\beta$-hydroxy steroid according to claim 6 which is 17$\alpha$-acetyl-17$\beta$-hydroxy-6,16-dimethyleneandrosta-4-en-3-one.

10. A 17$\beta$-hydroxy steroid according to claim 1 of the formula

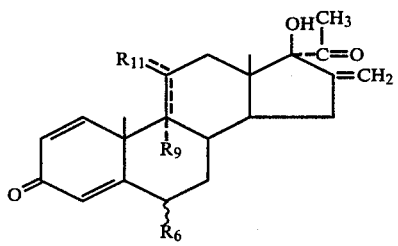 (VB)

where R$_6$, R$_9$, R$_{11}$, $\sim$ and ___ are defined in claim 1.

11. A 17$\beta$-hydroxy steroid according to claim 10 wherein R$_6$ is a hydrogen or fluorine atom.

12. A 17$\beta$-hydroxy steroid according to claim 11 which is 17$\alpha$-acetyl-17$\beta$-hydroxy-16-methyleneandrosta-1,4,9(11)-trien-3-one.

13. A 17$\beta$-hydroxy steroid according to claim 1 of the formula

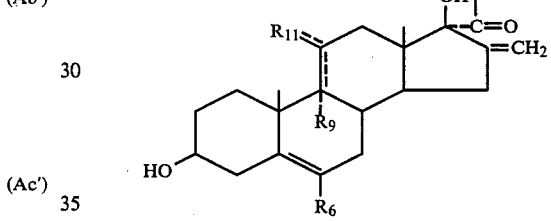 (VC)

and C$_3$ protected forms thereof where R$_6$, R$_9$, R$_{11}$, $\sim$ and ___ are defined in claim 1.

14. A 17$\beta$-hydroxy steroid according to claim 13 wherein the C$_3$ protecting group is selected from the group consisting of ethers or esters of the formula

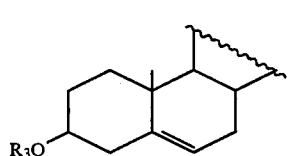 (Ca)

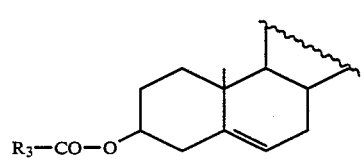 (Cb)

wherein R$_3$ is defined in claim 3.

15. A 17$\beta$-hydroxy steroid according to claim 14 where the C$_3$ protecting group is selected from the group consisting of methyl ether or acetate ester.

16. A sulfoxide selected from the group consisting of

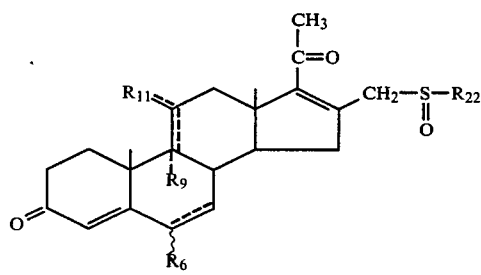
(VIAA)

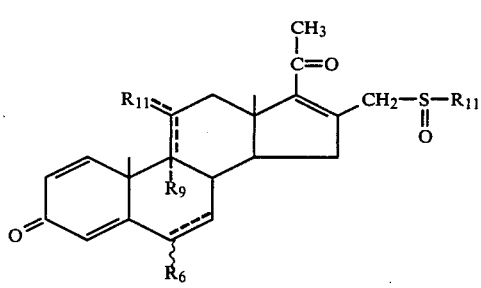
(VIB)

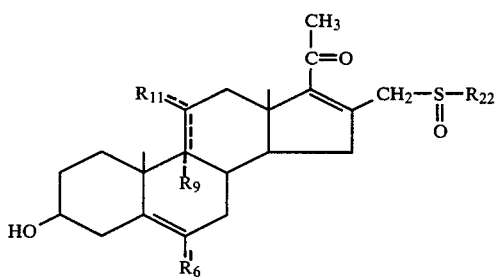
(VIC)

where $R_6$, $R_9$, $R_{10}$, $R_{11}$ and $\sim$ are defined in claim 1;

$R_{22}$ is alkyl of 1 thru 5 carbon atoms, trichloromethyl, phenyl, phenyl substituted with 1 thru 4 carbon atoms or substituted with 1 thru 3 nitro or trifluoromethyl groups, aralkyl of 7 thru 12 carbon atoms, or —N—($R_{122}$)$_2$;

$R_{122}$ is alkyl of 1 thru 4 carbon atoms, phenyl or phthalimide.

17. A sulfoxide according to claim 16 of the formula

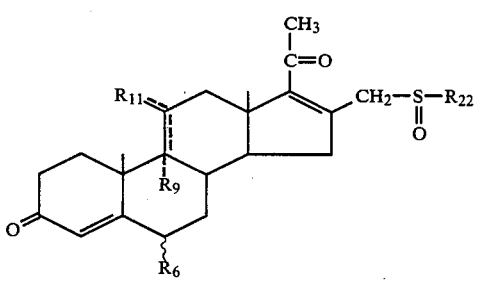
(VIAA)

and $C_3$ protected forms thereof where $R_{22}$ is defined in claim 16, $R_6$, $R_9$, $R_{11}$, $\sim$ and ___ are defined in claim 1.

18. A sulfoxide according to claim 17 where the $C_3$ protecting group is selected from the group consisting of enol ethers, ketals or enamines of the formula

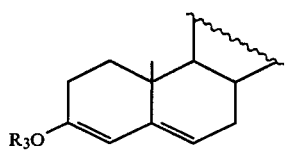
(Aa')

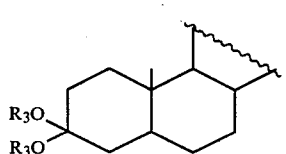
(Ab')

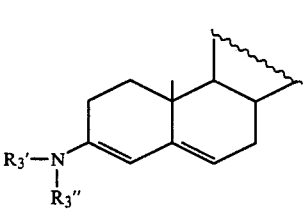
(Ac')

wherein $R_3$, $R_3'$ and $R_3''$ are defined in claim 3.

19. A sulfoxide according to claim 18 where the $C_3$ protecting group is selected from the group consisting of methyl enol ether, ethyl enol ether, ethylene ketal, and pyrolidine enamine.

20. A sulfoxide according to claim 19 where $R_{10}$ is a methyl group.

21. A sulfoxide according to claim 17 where $R_6$ is a hydrogen atom, methyl or methylene group.

22. A sulfoxide according to claim 16 which is 16-(phenylsulfinylmethyl)pregna-4,9(11),16-triene-3,20-dione.

23. A sulfoxide according to claim 16 which is 6-methyl-16-(phenylsulfinylmethyl)pregna-4,6,16-triene-3,20-dione.

24. A sulfoxide according to claim 16 which is 6-methylene-16-(phenylsulfinylmethyl)pregna-4,16-diene-3,20-dione.

25. A sulfoxide according to claim 16 of the formula

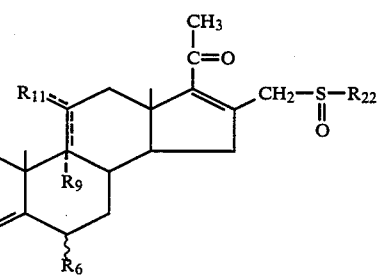
(VIB)

where $R_{22}$ is defined in claim 32, $R_6$, $R_{11}$, $\sim$ and ___ are defined in claim 1.

26. A sulfoxide according to claim 25 where $R_6$ is a hydrogen fluorine atom.

27. A sulfoxide according to claim 26 which is 16-(phenylsulfinylmethyl)pregna-1,4,9(11),16-tetraene-3,20-dione.

28. A sulfoxide according to claim 16 of the formula

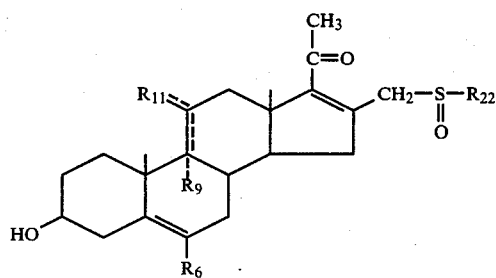

and C₃ protected forms thereof where $R_{22}$ is defined in claim 32, $R_6$, $R_9$, $R_{11}$, $\sim$ and ___ are defined in claim 1.

29. A sulfoxide according to claim 28 where the $C_3$ protecting group is selected from the group consisting of ethers or esters of the formula

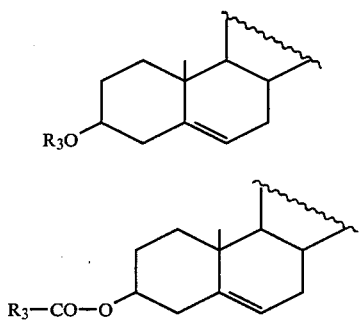

wherein $R_3$ is defined in claim 3.

30. A sulfoxide according to claim 27 where the $C_3$ protecting group is selected from the group consisting of methyl ether or acetate ester.

31. A 16-methylene-17α-hydroxy progesterone selected from the group consisting of

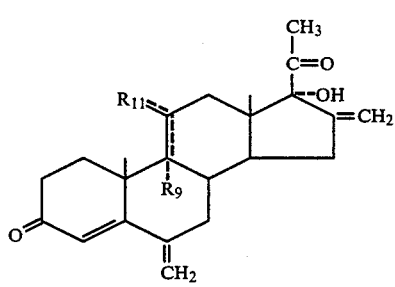

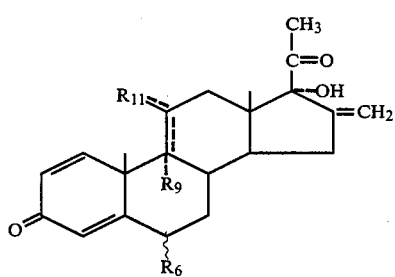

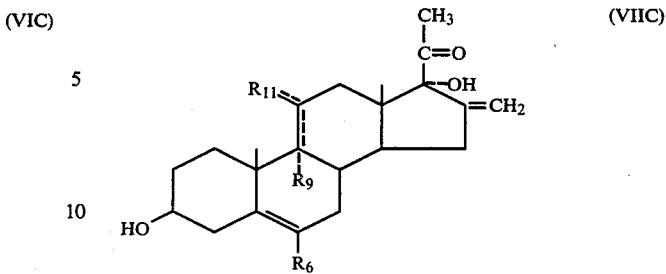

where $R_6$, $R_9$, $R_{11}$, $\sim$ and ___ are defined in claim 1.

32. A 16-methylene-17α-hydroxyprogesterone according to claim 31 of the formula

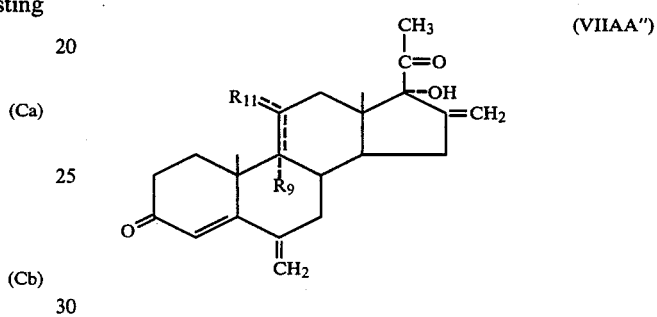

where $R_9$, $R_{11}$ and ___ are defined in claim 1.

33. A 16-methylene-17α-hydroxyprogessterone according to claim 32 where $R_{10}$ is a methyl group.

34. A 17α-hydroxy-16-methylene steroid according to claim 33 which is 17α-hydroxy-6,16-dimethylene-pregna-4-ene-3,20-dione.

35. 17α-hydroxy-6,16-dimethylenepregna-4-ene-3,20-dione 17-acetate.

36. 17α-hydroxy-16-methylenepregna-1,4,9(11)-triene-3,20-dione.

37. A process for the preparation of a 17β-hydroxy steroid of the formula

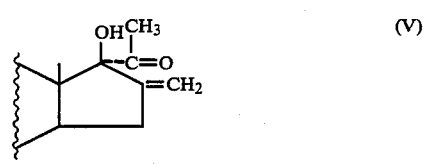

which comprises contacting a 17α-ethynyl steroid of the formula

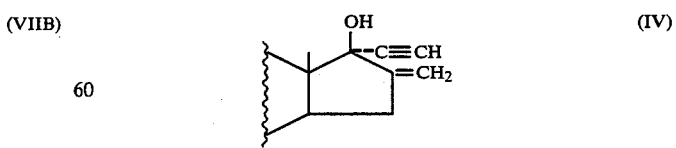

with a mercuric agent.

38. A process according to claim 37 where the 17α-ethynyl steroid starting material is selected from the group consisting of

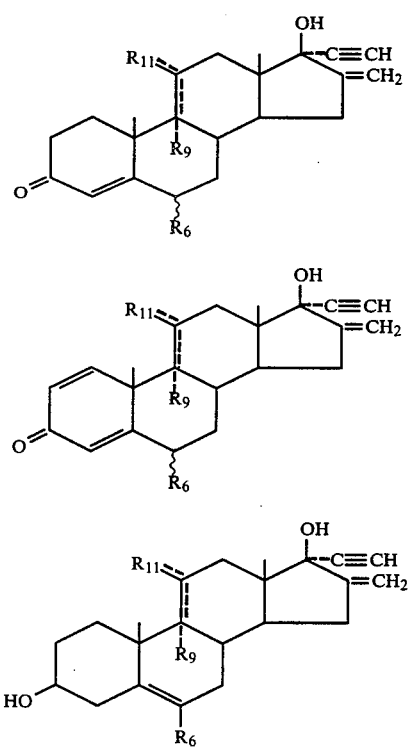

and C$_3$ protected forms thereof where R$_6$, R$_9$, R$_{11}$, ~, and ___ are defined in claim 1.

39. A process according to claim 38 where the C$_3$ protecting group for the Δ$^4$-3-keto steroid (A) is selected from the group consisting of enol ethers, ketals or enamines and for the 3β-hydroxy steroid (C) is an ether or ester of the formula

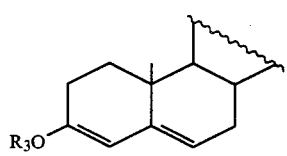

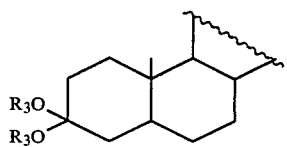

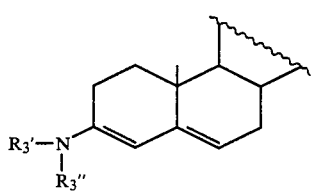

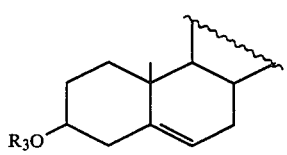

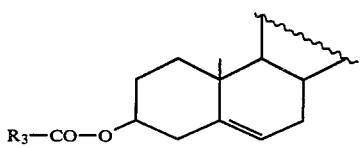

wherein R$_3$, R$_3'$, and R$_3''$ are defined in claim 3.

40. A process according to claim 39 where the C$_3$ protecting group is selected from the group consisting of methyl enol ether, ethyl enol ether, ethylene ketal, pyrrolidine enamine, methyl ester, ethyl ester, and acetal ester.

41. A process according to claim 37 where the mercuric agent is selected from the group consisting of mercuric sulfate, or mercuric ion attached to a sulfonic resin.

42. A process according to claim 37 where the mercuric agent is mercuric sulfate produced by the reaction of mercuric oxide and sulfuric acid.

43. A process according to claim 37 where catalytic amounts of mercuric agent are used.

44. A process according to claim 37 where the reaction temperature is 25°–100°.

45. A process according to claim 37 where the 17β-hydroxy steroid is 17α-acetyl-17β-hydroxy-16-methyleneandrosta-4,9(11)-dien-3-one.

46. A process according to claim 37 where the 17β-hydroxy steroid (V) is 17α-acetyl-17β-hydroxy-16-methyleneandrosta-1,4,9(11)-trien-3-one.

47. A process according to claim 37 where the 17β-hydroxy steroid (V) is 17α-acetyl-17β-hydroxy-6-methyl-16-methyleneandrosta-4,6-dien-3-one.

48. A process according to claim 37 where the 17β-hydroxy sterid (V) is 17α-acetyl-17β-hydroxy-6,16-dimethyleneandrosta-4-en-3-one.

49. A process for the preparation of a sulfoxide of the formula

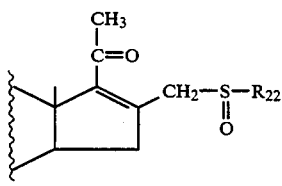

which comprises contacting a 17β-steroid of the formula

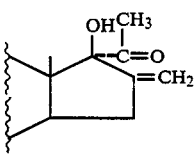

in a solvent containing a weak base or tertiary amine at a temperature of less than 0° with a sulfenylating agent of the formula R$_{22}$-S-M where R$_{22}$ is defined in claim 16 and M is a chlorine or bromine atom or phenylsulfone, phthalimide or imidazole group.

50. A process according to claim 49 where the 17β-hydroxy steroid (V) starting material selected from the group consisting of (VAA)

(VB)

(VC)

and C$_3$ protected forms thereof where R$_6$, R$_9$, R$_{11}$, and are defined in claim 1.

51. A process according to claim 50 where the C$_3$ protecting group for the Δ$^4$-3-keto steroid (A) is selected from the group consisting of enol ethers, ketals or enamines and for the 3β-hydroxy steroid (C) is an ether or ester of the formula (Aa')

(Ab')

(Ac')

(Ca)

(Cb)

wherein R$_3$, R$_3'$, and R$_3''$ are defined in claim 3.

52. A process according to claim 51 where the C$_3$ protecting group is selected from the group consisting of methyl enol ether, ethyl enol ether, ethylene ketal, pyrrolidine enamine, methyl ester, ethyl ester and acetate ester.

53. A process according to claim 49 where the solvent is selected from the group consisting of methylene chloride, chloroform, THF, dioxane, toluene, diethyl ether and mixtures thereof.

54. A process according to claim 49 where the solvent is methylene chloride.

55. A process according to claim 49 where the weak base is selected from the group consisting of trimethylamine, triethylamine, N-methylpiperidine.

56. A process according to claim 49 where the reaction temperature is from about −0° to about −80°.

57. A process according to claim 49 where the reaction temperature is from about −20° to about −55°.

58. A process according to claim 49 where the sulfoxide (VI) is 16-(phenylsulfinylmethyl)pregna-4,9(11),16-triene-3,20-dione.

59. A process according to claim 49 where the sulfoxide (VI) is 16-(phenylsulfinylmethyl)pregna-1,4,9(11),16-tetraene-3,20-dione.

60. A process according to claim 49 where the sulfoxide (VI) is 6-methyl-16-(phenylsulfinylmethyl)pregna-4,6,16-triene-3,20-dione.

61. A process according to claim 49 where the sulfoxide (VI) is 6-methylene-16-(phenylsulfinylmethyl)pregna-4,16-diene-3,20-dione.

62. A process for the preparation of a 16-methylene-17α-hydroxy progesterone of the formula (VII)

which comprises contacting a sulfoxide of the formula

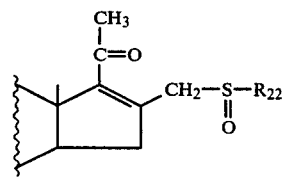 (VI)

with a thiophile at a temperature of greater than 30° under pressure where $R_{22}$ is defined in claim 16.

63. A process according to claim 62 where the sulfoxide (VI) starting material is selected from the group consisting of

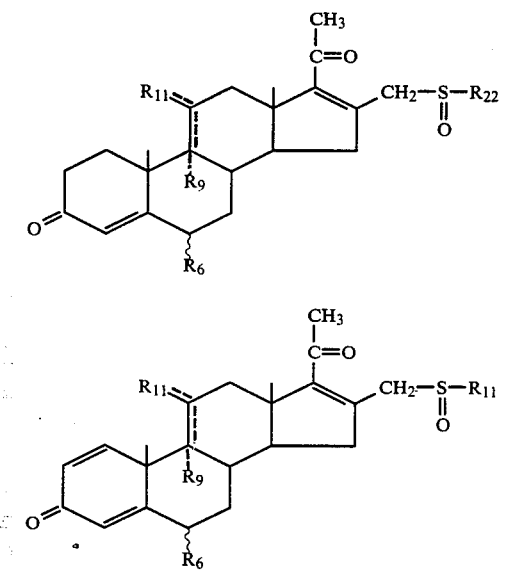

(VIAA)

(VIB)

(VIC)

and $C_3$ protected forms thereof where $R_{22}$ is defined in claim 32 and where $R_6$, $R_9$, $R_{11}$, and are defined in claim 1.

64. A process according to claim 63 where the $C_3$ protecting group for the $\Delta^4$-3-keto steroid (A) is selected from the group consisting of enol ethers, ketals or enamines and for the 3β-hydroxy steroid (C) is an ether or ester of the formula

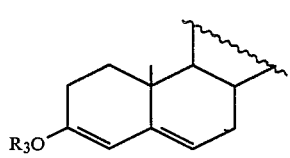

(Aa')

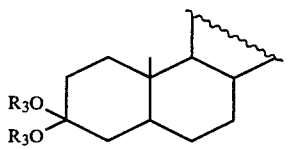 (Ab')

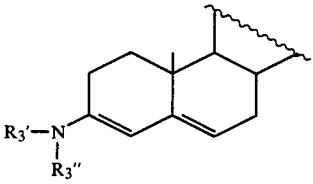 (Ac')

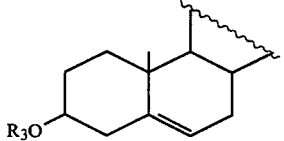 (Ca)

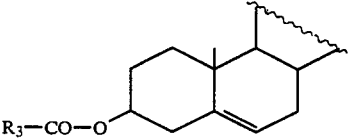 (Cb)

wherein $R_3$, $R_3'$, and $R_3''$ are defined in claim 3.

65. A process according to claim 63 where the $C_3$ protecting group for the $\Delta^4$-3-keto steroid (A) is selected from the group consisting of methyl enol ether, ethyl enol ether, ethylene ketal, pyrrolidine enamine and for the 3β-hydroxy steroid (C) is 3-ethoxy ethyl ester or dihydropyranyl ether.

66. A process according to claim 62 where the thiophile is selected from the group consisting of trimethylphosphite, triethylphosphite and tributylphosphite.

67. A process acccording to claim 62 where the thiophile is trimethylphosphite.

68. A process according to claim 62 where the reaction temperature is from about 50° to 100°.

69. A process according to claim 62 where the 16-methylene-17α-hydroxyprogesterone (VII) is 17α-hydroxy-16-methylenepregna-4,9(11)-diene-3,20-dione.

70. A process according to claim 62 where the 16-methylene-17α-hydroxyprogesterone (VII) is 17α-hydroxy-16-methylenepregna-1,4,9(11)-triene-3,20-dione.

71. A process according to claim 62 where the 16-methylene-17α-hydroxyprogesterone (VII) is 17α-hydroxy-6-methyl-16-methylenepregna-4,6-diene-3,20-dione.

72. A process according to claim 62 where the 16-methylene-17α-hydroxyprogesterone (VII) is 17α-hydroxy-6,16-dimethylenepregna-4-ene-3,20-dione.

73. 17α,21-Dihydroxy-16-methylenepregna-1,4,9(11)-triene-3,20-dione 21-acetate.

74. A 17-ethynyl steroid which is 17α-ethynyl-17β-hydroxy-16-methyleneandrost-4-en-3-one.

75. A sulfoxide according to claim 16 which is 16-(phenylsulfinylmethyl)-pregn-4,16-diene-3,20-dione.

76. 17α-Hydroxy-3β-methoxy-16-methylenepregna-3,5-diene-20-one.

77. A process for preparation of a 17β-hydroxy steroid according to claim 37 which is 17α-acetyl-17β-hydroxy-16-methyleneandrost-4-ene-3-one.

78. A process for the preparation of a sulfoxide according to claim 49 which is 16-(phenylsulfinylmethyl)-pregn-4,16-dien-3,20-dione.

79. A process for the preparation of a 16-methylene-17α-hydroxy progesterone according to claim 62 which is 17α-hydroxy-3β-methoxy-16-methylenepregna-3,5-dien-20-one.

* * * * *

UNITED STATES PATENT OFFICE
CERTIFICATE OF CORRECTION

Patent No. 4,567,001           Dated January 28, 1986

Inventor(s) Verlan H. VanRheenen

It is certified that error appears in the above-identified patent and that said Letters Patent are hereby corrected as shown below:

Column 28, line 66, "____ is" should read --.... is--
Column 29, line 14, "and ...." should read --and ....--
Column 29, line 61, "claim 16" should read --claim 6--
Column 30, line 14, "and ____" should read --and ....--
Column 30, line 39, "and ____" should read --and ....--
Column 31, line 38, "and ____" should read --and ....--

Column 31, line 59, "  " should read --  --

Column 32, line 31, "claim 19" should read --claim 17--
Column 32, line 59, "and ____" should read --and ....--
Column 32, line 59, "claim 32" should read --claim 16--
Column 33, line 16, "claim 32" should read --claim 16--
Column 33, line 16, "and ____" should read --and ....--
Column 34, line 14, "and ____" should read --and ....--
Column 34, line 31, "and ____" should read --and ....--

Column 35, line 9, "  " should read --  --

Column 35, line 33, "and ____" should read --and ....--

Column 37, line 13, "  " should read --  --

Column 37, line 37, "$R_{11}$, and" should read --$R_{11}$, $\sim$ and--
Column 37, line 38, "are" should read --.... are--

UNITED STATES PATENT OFFICE
CERTIFICATE OF CORRECTION

Patent No. 4,567,001  Dated January 28, 1986

Inventor(s) Verlan H. VanRheenen

It is certified that error appears in the above-identified patent and that said Letters Patent are hereby corrected as shown below:

Column 39, line 25, "  " should read -- (structure) --

Column 39, line 53, "$R_{11}$, and" should read --$R_{11}$, ~ and--
Column 39, line 53, "and are" should read --and .... are--
Column 40, line 55, "steroid which" should read --steroid according to claim 2 which--
Column 39, line 53, "claim 32" should read --claim 16--

Signed and Sealed this

Thirteenth Day of January, 1987

*Attest:*

DONALD J. QUIGG

*Attesting Officer*   *Commissioner of Patents and Trademarks*

UNITED STATES PATENT OFFICE
CERTIFICATE OF CORRECTION

Patent No. 4,567,001         Dated January 28, 1986

Inventor(s) Verlan H. VanRheenen

It is certified that error appears in the above-identified patent and that said Letters Patent are hereby corrected as shown below:

Column 2, line 60 "16α- or 16α-methyl-" should read --16α- or 16β-methyl- --
Column 11, line 20 "____ is a singel" should read -- .... is a single--
Column 11, line 46 "futher" should read --further--
Column 12, line 30 "(IIBA)" should read --(IIB)--
Column 12, line 66 "(0.2 ml)" should read --(.2 ml)--
Column 15, line 62 "equal to 31 55°" should read -- equal to -55° --
Column 16, line 37 "2.47, 2.47, 5.12" should read -- 2.47, 5.12 --
Column 19, line 30 "≤-68°." should read -- ≤-68°. --
Column 23, line 42 "-methylenepregna-" should read -- -methylenepregn- --
Column 23, line 59 "diene-" should read -- dien- --

Signed and Sealed this

Fifth Day of January, 1988

Attest:

DONALD J. QUIGG

Attesting Officer   Commissioner of Patents and Trademarks